(12) United States Patent  
Leibler et al.

(10) Patent No.: US 10,060,050 B2  
(45) Date of Patent: Aug. 28, 2018

(54) COMPOUND LIBRARY PREPARATION PROCESS

(71) Applicant: ECOLE SUPERIEURE DE PHYSIQUE ET DE CHIMIE INDUSTRIELLES DE LA VILLE DE PARIS, Paris (FR)

(72) Inventors: Ludwik Leibler, Paris (FR); Renaud Nicolay, Verrieres-le-Buisson (FR)

(73) Assignee: ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 0 days.

(21) Appl. No.: 15/242,931

(22) Filed: Aug. 22, 2016

(65) Prior Publication Data

US 2017/0050163 A1 Feb. 23, 2017

(30) Foreign Application Priority Data

Aug. 20, 2015 (FR) ..................................... 15 57821

(51) Int. Cl.
| | |
|---|---|
| *C40B 50/04* | (2006.01) |
| *C07F 5/02* | (2006.01) |
| *C07F 5/04* | (2006.01) |
| *B01J 19/00* | (2006.01) |
| *C40B 40/04* | (2006.01) |

(52) U.S. Cl.
CPC ........... *C40B 50/04* (2013.01); *B01J 19/0046* (2013.01); *C07F 5/025* (2013.01); *C07F 5/04* (2013.01); *B01J 2219/0072* (2013.01); *B01J 2219/00599* (2013.01); *C40B 40/04* (2013.01)

(58) Field of Classification Search
CPC ............. C40B 50/04; C07F 5/04; C07F 5/025
See application file for complete search history.

(56) References Cited

U.S. PATENT DOCUMENTS 5,288,707 A * 2/1994 Metternich ........ C07K 5/06191  
514/14.9  
2009/0018357 A1* 1/2009 Pinchuk .................. C07F 9/106  
554/77

FOREIGN PATENT DOCUMENTS

WO WO 2012/073038 A2 6/2012

OTHER PUBLICATIONS

Ramstrom et al. Biochimica et Biophysica Acta 2002, 1572, 178-186.*
Roy et al. J. Organomet. Chem. 2007, 692, 784-790.*
Beeren et al. Dynamic Combinatorial Chemistry, 2010, Chapter 1, pp. 1-22.*
Rasmussen et al. Organic Synthesis and Molecular Engineering, Chapter 14: Dynamic Combinatorial Chemistry, 2014, pp. 393-436.*
Ali et al. Arch. Pharm. 2004, 337, 193-197.*
Brooks et al. Chem. Commun. 1967, 18, 952-953.*
Baltus et al., "Olefin cross-metathesis/Suzuki-Miyaura reactions on vinylphenylboronic acid pinacol esters," Tetrahedron Letters, vol. 54, No. 10, 2013 (Available online Dec. 28, 2012), pp. 1211-1217, XP028968428.
Demetriades et al., "Dynamic Combinatorial Chemistry Employing Boronic Acids/Boronate Esters Leads to Potent Oxygenase Inhibitors," Angewandte Chemie International Edition, vol. 51, No. 27, Jul. 2, 2012 (Published online May 25, 2012), pp. 6672-6675, XP055272020.
Demetriades et al., "Dynamic Combinatorial Chemistry Employing Boronic Acids/Boronate Esters Leads to Potent Oxygenase Inhibitors," Supporting Information, Angewandte Chemie, May 25, 2012, pp, 1-52 (53 pages total), XP055272030.
French Preliminary Report and Written Opinion for French Application No. 1557821, dated May 17, 2016.
Herrmann, "Dynamic mixtures and combinatorial libraries: imines as probes for molecular evolution at the interface between chemistry and biology," Organic & Biomolecular Chemistry, vol. 7, 2009 (Published on the web Jun. 29, 2009), pp. 3195-3204.
Ramström et al., "Drug Discovery by Dynamic Combinatorial Libraries," Nature Reviews Drug Discovery, vol. 1, Jan. 2002, pp. 26-36.
Schmidt et al., "Dynamic template-assisted strategies in fragment-based drug discovery," Trends in Biotechnology, vol. 27, No. 9, 2009, pp. 512-521.

* cited by examiner

*Primary Examiner* — Matthew P Coughlin
(74) *Attorney, Agent, or Firm* — Birch, Stewart, Kolasch & Birch, LLP

(57) ABSTRACT

The present invention relates to the preparation of a compound library comprising the following steps:
  i. Having available at least two different compounds each comprising at least a dioxaborolane or dioxaborinane ring. In said compounds:
    the boron of the dioxaborolane or dioxaborinane ring is directly linked to a carbon atom of a hydrocarbon radical;
    at least one carbon atom of the dioxaborolane or dioxaborinane ring is monosubstituted, the other carbon atoms of the dioxaborolane or dioxaborinane ring being non-substituted or monosubstituted;
    in at least two compounds, the hydrocarbon radicals linked to the boron are different;
    in at least two compounds, the substituents carried by at least one of the carbon atoms of the dioxaborolane or dioxaborinane rings are different and/or the size of the boronic ester ring is different;
  ii. Reacting the compounds of step (i.) and forming, by a boronic ester metathesis reaction, the library comprising at least four different compounds.
The present invention also relates to a compound library.

18 Claims, 7 Drawing Sheets

COMPOUND LIBRARY PREPARATION PROCESS

The present invention relates to the preparation of a compound library.

In the search for new active molecules, whether the activity is in the therapeutic or non-therapeutic domain, processes are always sought to enable the synthesis, in a controlled manner, of a large number of compounds and so to test the activity of a large number of compounds.

The discovery of new bioactive substances, and more particularly of molecules presenting specific properties with a view to a precise therapeutic application, is based on the use of various strategies, including the serial synthesis of individual molecules subject to tests, one after the other or collectively, notably of their potential activity on a given biological target. The need to rapidly and productively discover molecules with new useful properties has led in this way to the development of combinatorial chemistry. Combinatorial chemistry implies the rapid synthesis of a large number of molecules. This collection of molecules, also called a library, can be a chemical mixture of components or a set of individual pure compounds. This library is then subjected to screening for a biological activity, enabling any active components to be identified. To put it simply, the combinatorial approach is therefore characterised by two principal steps: the synthesis of the library and the identification of the active component.

The basic idea in a library is to carry out reactions with several starting materials at once, generating a library with a large population of components from a smaller number of starting materials.

It is now also known to test the activity of a library of compounds, in particular peptides, by testing the affinity of several fragments and the interaction of fragments among themselves, with respect to one or more target proteins (1, 2, 3).

In this way, the synthesis of compound libraries is an important step in the development processes of a new drug. Other examples of applications include the optimisation of molecular properties, for example for the identification of catalysts.

SUMMARY OF THE INVENTION

Unexpectedly, a new, rapid boronic ester metathesis reaction has been discovered that can be carried out at ambient temperature, with or without catalyst, enabling new compounds to be easily prepared. Furthermore, the reaction is advantageously quantitative.

Schematically, the boronic ester metathesis reaction may be represented as follows:

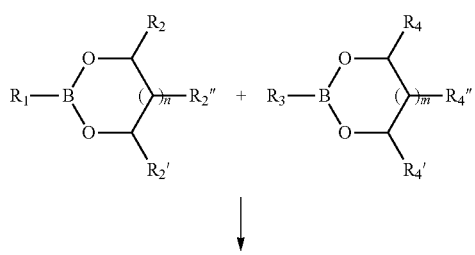

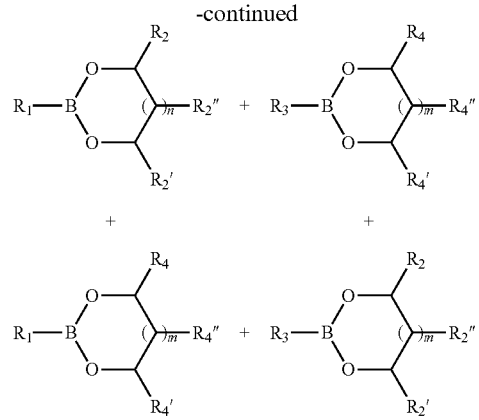

The object of the invention is a process, comprising the preparation of a compound library, characterised in that the library is prepared by a process comprising the following steps:
  i. Having available at least two different compounds each comprising at least a dioxaborolane or dioxaborinane ring, forming a boronic ester function. In said compounds:
    the boron of the dioxaborolane or dioxaborinane ring is directly linked to a carbon atom of a hydrocarbon radical;
    at least one carbon atom of the dioxaborolane or dioxaborinane ring is monosubstituted, the other carbon atoms of the dioxaborolane or dioxaborinane ring being non-substituted or monosubstituted;
    in at least two compounds, the hydrocarbon radicals linked to the boron are different;
    in at least two compounds, the substituents carried by at least one of the carbon atoms of the dioxaborolane or dioxaborinane rings are different and/or the size of the boronic ester ring is different;
  ii. Reacting the compounds of step (i.) and forming, by a boronic ester metathesis reaction, the library comprising at least four different compounds, each having at least one substituents of a dioxaborolane or dioxaborinane ring different and/or a boronic ester ring of a different size compared to another compound.

Another object of the invention is a compound library comprising more than two different compounds, each comprising at least one dioxaborolane or dioxaborinane ring. In said compounds:
  the boron of the dioxaborolane or dioxaborinane group is directly linked to a carbon atom of a hydrocarbon radical;
  at least one carbon atom of the dioxaborolane or dioxaborinane ring is monosubstituted, the other carbon atoms of the dioxaborolane or dioxaborinane ring being non-substituted or monosubstituted;
  in at least two compounds, the hydrocarbon radicals linked to the boron are different;
  in at least two compounds, the substituents carried by at least one of the carbon atoms of the dioxaborolane or dioxaborinane rings are different and/or the size of the boronic ester ring is different.

DEFINITIONS

Figure 1:
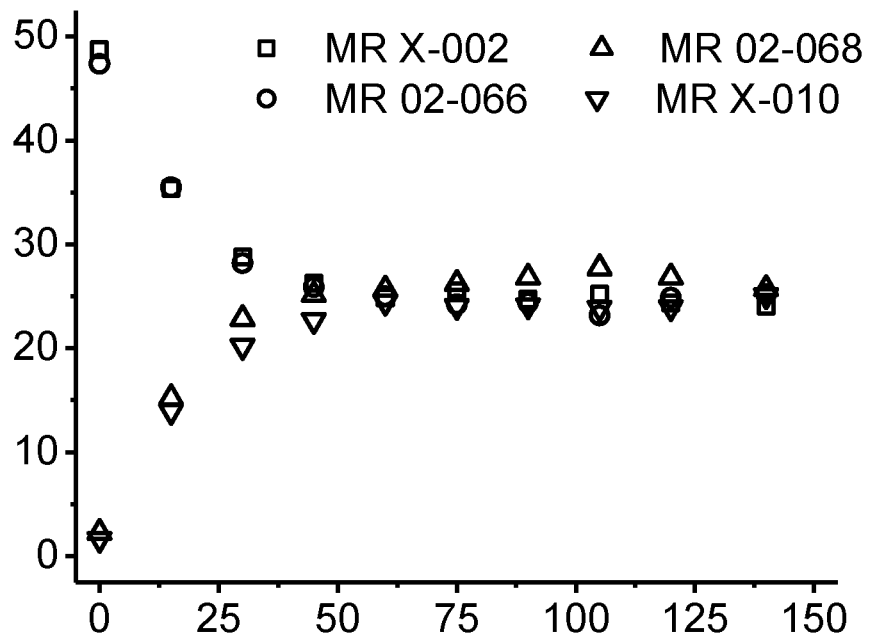
FIG. 1. Evolution of the molar percentage (ordinate; without unit) of the different boronic esters as a function of time (abscissa; minutes) during the metathesis of two phenylboronic esters in anhydrous hexane at 5° C.

"Dioxaborolane" according to the present invention designates a group of formula:

"Dioxaborinane" according to the present invention designates a group of formula:

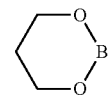

"Boronic ester" according to the present invention designates compounds comprising a dioxaborolane or dioxaborinane group. "Boronic ester" may also designate the function —O—B—O—.

According to the present invention, "boronic ester ring" may also designate the groups dioxaborolane and dioxaborinane. The size of the boronic ester ring designates the number of atoms in the ring.

Substituents on the dioxaborolane and dioxaborinane rings according to the present invention designate the groups carried by the carbon and boron atoms that constitute the dioxaborolane and dioxaborinane rings.

According to the present invention, "hydrocarbon" designates any radical comprising atoms of carbon and hydrogen. This group may also include heteroatoms and/or be substituted by halogens. The hydrocarbon group preferably includes 1-50, more preferably 1-18, still more preferably 1-12 carbon atoms.

"Heteroatom" according to present invention designates atoms of sulfur, nitrogen, oxygen, boron, phosphorus or silicon.

"Halogen atom" or "halogen" according to present invention designates atoms of fluorine, chlorine, bromine or iodine.

The "hydrocarbon" group may include ester, amide, ether, thioether, secondary or tertiary amine, carbonate, urethane, carbamide, anhydride or boronic ester functions. If applicable, the "hydrocarbon" group may be substituted, once or several times, notably by a halogen or an —Rz, —OH, —NH$_2$, —NHRz, —NRzR'z, —C(O)—H, —C(O)—Rz, —C(O)—OH, —C(O)—O—Rz, —O—C(O)—Rz, —O—C(O)—O—Rz, —O—C(O)—N(H)—Rz, —N(H)—C(O)—O—Rz, —O—Rz, —SH, —S—Rz, —S—S—Rz, —CO—NH$_2$, —C(O)—N(H)—Rz, —C(O)—NRzR'z, —N(H)—C(O)—Rz, —N(Rz)-C(O)—Rz', —CN, —NCO, —NCS or boronic ester group, with Rz and R'z, identical or different, representing a $C_1$-$C_{50}$ alkyl radical, a $C_2$-$C_{50}$ alkenyl radical, a $C_2$-$C_{50}$ alkynyl radical, a $C_1$-$C_{50}$ halogenoalkyl radical or a $C_1$-$C_{50}$ heteroalkyl radical.

An "alkyl" group according to the present invention designates a monovalent, saturated, linear or branched hydrocarbon chain, preferably comprising 1-50 carbon atoms, more preferably 1-18 carbon atoms, still more preferably 1-12 carbon atoms. As examples, methyl, ethyl, propyl, isopropyl, butyl, isobutyl, sec-butyl, tert-butyl, pentyl or hexyl groups may be mentioned. If applicable, the alkyl group may be substituted.

An "alkenyl" group according to the present invention designates a monovalent, linear or branched hydrocarbon chain, comprising at least one double bond and preferably comprising 2-50 carbon atoms, more preferably 2-18 carbon atoms, still more preferably 2-12 carbon atoms. As examples, ethenyl, propenyl, butenyl, pentenyl and hexenyl groups may be mentioned. If applicable, the alkenyl group may be substituted.

An "alkynyl" group according to the present invention designates a monovalent, linear or branched hydrocarbon chain, comprising at least one triple bond and comprising 2-50 carbon atoms, more preferably 2-18 carbon atoms, still more preferably 2-12 carbon atoms. As examples, ethynyl or propynyl groups may be mentioned. If applicable, the alkynyl group may be substituted.

"Halogenoalkyl" according to the present invention designates an alkyl, alkenyl or alkynyl group as defined above in which one or more hydrogen atoms have been replaced by a halogen atom as defined above. This may be a —$CF_3$ group in particular.

"Heteroalkyl" according to the present invention designates an alkyl, alkenyl or alkynyl group as defined previously substituted by at least one heteroatom.

If applicable, an alkyl, alkenyl, alkynyl, halogenoalkyl or heteroalkyl group may be substituted, once or several times, notably by a halogen or an —Rz, —OH, —$NH_2$, —NHRz, —NRzR'z, —C(O)—H, —C(O)—Rz, —C(O)—OH, —C(O)—O—Rz, —O—C(O)—Rz, —O—C(O)—O—Rz, —O—C(O)—N(H)—Rz, —N(H)—C(O)—O—Rz, —O—Rz, —SH, —S—Rz, —S—S—Rz, —CO—$NH_2$, —C(O)—N(H)—Rz, —C(O)—NRzR'z, —N(H)—C(O)—Rz, —N(Rz)-C(O)—Rz', —CN, —NCO, —NCS or boronic ester group, with Rz and R'z, identical or different, representing a $C_1$-$C_{50}$ alkyl radical, a $C_2$-$C_{50}$ alkenyl radical, a $C_2$-$C_{50}$ alkynyl radical, a $C_1$-$C_{50}$ halogenoalkyl radical or a $C_1$-$C_{50}$ heteroalkyl radical.

A "cycloalkyl" group according to the present invention designates a cyclical hydrocarbon chain, which may be saturated or unsaturated but not aromatic, preferably comprising 3-18 carbon atoms in the ring. Examples include cyclopropyl, cyclopentyl, cyclohexyl, cycloheptyl and cyclooctyl groups. If applicable, the cycloalkyl group may be substituted, once or several times, notably by a halogen or an —Rz, —OH, —$NH_2$, —NHRz, —NRzR'z, —C(O)—H, —C(O)—Rz, —C(O)—OH, —C(O)—O—Rz, —O—C(O)—Rz, —O—C(O)—O—Rz, —O—C(O)—N(H)—Rz, —N(H)—C(O)—O—Rz, —O—Rz, —SH, —S—Rz, —S—S—Rz, —CO—$NH_2$, —C(O)—N(H)—Rz, —C(O)—NRzR'z, —N(H)—C(O)—Rz, —N(Rz)-C(O)—Rz', —CN, —NCO, —NCS or boronic ester group, with Rz and R'z, identical or different, representing a $C_1$-$C_{50}$ alkyl radical, a $C_2$-$C_{50}$ alkenyl radical, a $C_2$-$C_{50}$ alkynyl radical, a $C_1$-$C_{50}$ halogenoalkyl radical or a $C_1$-$C_{50}$ heteroalkyl radical.

A "polycycloalkyl" group according to the present invention designates a saturated hydrocarbon chain comprising 5-50 carbon atoms and comprising at least 2, preferably 2 or 3, fused rings. As an example, the adamantyl group may be mentioned. If applicable, the cycloalkyl group may be substituted, once or several times, notably by a halogen or an —Rz, —OH, —$NH_2$, —NHRz, —NRzR'z, —C(O)—H, —C(O)—Rz, —C(O)—OH, —C(O)—O—Rz, —O—C(O)—Rz, —O—C(O)—O—Rz, —O—C(O)—N(H)—Rz, —N(H)—C(O)—O—Rz, —O—Rz, —SH, —S—Rz, —S—S—Rz, —CO—$NH_2$, —C(O)—N(H)—Rz, —C(O)—NRzR'z, —N(H)—C(O)—Rz, —N(Rz)-C(O)—Rz', —CN, —NCO, —NCS or boronic ester group, with Rz and R'z, identical or different, representing a $C_1$-$C_{50}$ alkyl radical, a $C_2$-$C_{50}$ alkenyl radical, a $C_2$-$C_{50}$ alkynyl radical, a $C_1$-$C_{50}$ halogenoalkyl radical or a $C_1$-$C_{50}$ heteroalkyl radical.

"Cycloheteroalkyl" according to the present invention designates a monocycle or a polycycle (comprising fused, linked or spiro rings), as defined previously and comprising one or more heteroatoms, preferably 1-4 heteroatoms, more preferably 1 or 2 heteroatoms, such as for example atoms of sulfur, nitrogen, oxygen or silicon. It may notably be a pyrrolidinyl, piperidinyl, piperazinyl or morpholinyl group.

"Polycycloheteroalkyl" according to the present invention designates a saturated hydrocarbon chain comprising 5-50 carbon atoms and comprising at least 2, preferably 2 or 3, fused rings, of which at least one is a cycloheteroalkyl. At least one of the rings may be substituted as described previously.

"Aliphatic ring" according to the present invention designates a "cycloalkyl", "polycycloalkyl", "cycloheteroalkyl" or "polycycloheteroalkyl" group as defined previously.

"Aryl" according to the present invention designates an aromatic hydrocarbon group. The aryl group may include heteroatoms; in this case it is called a "heteroaryl" radical. The term "aryl" includes aralkyl and alkyl-aryl groups. The aromatic hydrocarbon group may be substituted, once or several times, notably by a halogen or an —Rz, —OH, —$NH_2$, —NHRz, —NRzR'z, —C(O)—H, —C(O)—Rz, —C(O)—OH, —C(O)—O—Rz, —O—C(O)—Rz, —O—C(O)—O—Rz, —O—C(O)—N(H)—Rz, —N(H)—C(O)—O—Rz, —O—Rz, —SH, —S—Rz, —S—S—Rz, —CO—$NH_2$, —C(O)—N(H)—Rz, —C(O)—NRzR'z, —N(H)—C(O)—Rz, —N(Rz)-C(O)—Rz', —CN, —NCO, —NCS or boronic ester group, with Rz and R'z, identical or different, representing a $C_1$-$C_{50}$ alkyl radical, a $C_2$-$C_{50}$ alkenyl radical, a $C_2$-$C_{50}$ alkynyl radical, a $C_1$-$C_{50}$ halogenoalkyl radical or a $C_1$-$C_{50}$ heteroalkyl radical. The term "aryl" covers groups that include ester, amide, ether, thioether, secondary or tertiary amine, carbonate, urethane, carbamide, anhydride or boronic ester functions.

"Alkyl-aryl" according to the present invention designates an alkyl, alkenyl or alkynyl group, as defined above, linked to the rest of the molecule through an aryl group, as defined above. The alkyl, alkenyl or alkynyl group may in addition comprise one or more heteroatoms or halogens.

"Aralkyl" according to the present invention designates an aryl group, as defined above, linked to the rest of the molecule through an alkyl, alkenyl or alkynyl chain, as defined above. As an example, the benzyl group may be mentioned. The alkyl, alkenyl or alkynyl group may in addition comprise one or more heteroatoms or halogens.

"Cycloheteroaryl" or "polycycloheteroaryl" according to the present invention designate a monocycle or a polycycle (comprising fused, linked or spiro rings), preferably comprising 5-10 atoms in the ring, more preferably 5-6 atoms in the ring, and comprising one or more heteroatoms, preferably 1-4 heteroatoms, more preferably 1 or 2 heteroatoms, such as for example atoms of sulfur, nitrogen, oxygen or silicon.

"Polyaryl" according to the present invention designates a group comprising at least two aryl groups as defined above. The groups may be fused or separated by a hydrocarbon radical.

"Aromatic ring" according to the present invention designates an "aryl", "heteroaryl", "cycloheteroaryl", "polycycloheteroaryl" or "polyaryl" group as defined previously.

"Small organic molecule" designates molecules of molecular mass less than 2000 g/mol, preferably less than 1500 g/mol, more preferably less than 1000 g/mol.

DETAILED DESCRIPTION OF THE INVENTION

The invention therefore relates to a process, comprising the preparation of a compound library, characterised in that the library is prepared by a process comprising the following steps:

i. Having available at least two different compounds each comprising at least a dioxaborolane or dioxaborinane ring, forming a boronic ester function. In said compounds:
- the boron of the dioxaborolane or dioxaborinane ring is directly linked to a carbon atom of a hydrocarbon radical;
- at least one carbon atom of the dioxaborolane or dioxaborinane ring is monosubstituted, the other carbon atoms of the dioxaborolane or dioxaborinane ring being non-substituted or monosubstituted;
- in at least two compounds, the hydrocarbon radicals linked to the boron are different;
- in at least two compounds, the substituents carried by at least one of the carbon atoms of the dioxaborolane or dioxaborinane rings are different and/or the size of the boronic ester ring is different;

ii. Reacting the compounds of step (i.) and forming, by a boronic ester metathesis reaction, the library comprising at least four different compounds, each having at least one substituents of a dioxaborolane or dioxaborinane ring different and/or a boronic ester ring of a different size compared to another compound.

The dioxaborolane or dioxaborinane ring forms a boronic ester function. In other words, these compounds each present at least one boronic ester function. Starting compounds each having several boronic ester functions, and so each having at least as many boron atoms as boronic ester functions, may be envisaged.

Preferably, the substituent(s) on the carbon atoms of the dioxaborolane or dioxaborinane ring is/are (a) hydrocarbon radical(s).

In particular, the library is prepared by a process comprising the following steps:

i. Having available at least two compounds each comprising at least a dioxaborolane or dioxaborinane ring, of formula (Ia) and (Ib)

ii. Reacting the compounds of step (i.) and forming, by a boronic ester metathesis reaction, the library comprising at least four compounds of formula (Ia), (Ib), (Ic) and (Id)

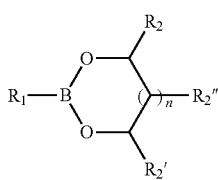

(Ia)

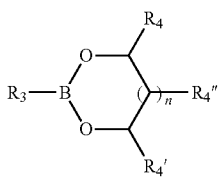

(Ib)

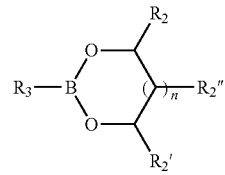

(Ic)

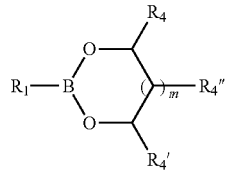

(Id)

Where
n=0 or 1
m=0 or 1
$R_1$ and $R_3$ are different and each represents a hydrocarbon radical; the atom of $R_1$ and $R_3$ linked to the boron is a carbon atom
$R_2$, $R_2'$, and $R_2''$, identical or different, each represents a hydrogen atom, a hydrocarbon radical, or form together an aliphatic or aromatic ring
$R_4$, $R_4'$, and $R_4''$, identical or different, each represents a hydrogen atom, a hydrocarbon radical, or form together an aliphatic or aromatic ring
If n=m then at least one of the substituents $R_4$, $R_4'$, and $R_4''$ is different from the substituents $R_2$, $R_2'$, and $R_2''$ Preferably, in step (i.), more than two compounds carrying at least one dioxaborolane or dioxaborinane and/or at least one compound carrying several dioxaborolane or dioxaborinane rings are available. In this way, a library is obtained that comprises more than three compounds, depending on the nature of the substituents on the starting compounds.

The reaction is advantageously quantitative. To illustrate this idea, this means that when all the substituents are different ($R_1$ different from $R_3$, sets of substituents {$R_2$, $R_2'$, $R_2''$} and {$R_4$, $R_4'$, $R_4''$} different) and only carry a single boronic ester function, starting from P different starting compounds, $P^2$ different compounds are obtained at the end of the reaction. As the reaction can be rapid and quantitative, these $P^2$ compounds are advantageously in stoichiometric quantities if the P starting compounds were present in stoichiometric quantities.

In a variant of the process, the reaction is carried out with more than two compounds (Ia) and (Ib) placed in the mixture and different from one another: by their different $R_1$ groups or their different $R_3$ groups; and by their different $R_2$, $R_2'$, $R_2''$ groups or their different $R_4$, $R_4'$, $R_4''$ groups.

The metathesis reaction enables the exchange of the sets of substituents {$R_2$, $R_2'$, $R_2''$} and {$R_4$, $R_4'$, $R_4''$}, linked to the carbon atoms of the ring, among themselves, and enables the exchange of the $R_1$ and $R_3$ groups, linked to the boron atom, among themselves. This enables the chemical nature (and even the size) of the compounds to be modified depending on those of the $R_1$ and $R_3$ groups linked to the boron atom and those of the sets of substituents {$R_2$, $R_2'$, $R_2''$} and {$R_4$, $R_4'$, $R_4''$}, this obviously being extendable to p different $R_1$ and $R_3$ groups linked to the boron atom (p greater than 2) and q sets of different substituents {$R_2$, $R_2'$, $R_2''$} and {$R_4$, $R_4'$, $R_4''$} linked to the carbon atoms of the boronic ester rings (with q greater than 2).

In the case in which the starting compounds are considered with the definition of the above paragraph and only comprise a single dioxaborolane or dioxaborinane ring, p×q different compounds are obtained for the library at the end of the reaction.

In a variant of the process, the reaction is carried out with at least one compound carrying several dioxaborolane or dioxaborinane rings are available. In particular, the compound can carry two, three or four dioxaborolane or dioxaborinane rings. In this case, the number given above does not apply.

Boronic Ester Metathesis Reaction

The reaction is preferably carried out in an organic medium, more preferably in a medium that is unfavourable to the hydrolysis of the boronic ester functions of the dioxaborolane or dioxaborinane rings. It is desirable to favour the metathesis reaction over any dissociation or dissociation and recombination reactions of the boronic ester functions.

A "medium that is unfavourable to hydrolysis of the boronic ester functions" designates an organic or aqueous medium and experimental conditions under which, when starting from boronic esters, the equilibrium between boronic esters and boronic acid+(1,2- or 1,3-) diol is shifted towards the boronic ester form. "Equilibrium shifted towards the boronic ester form" designates that the molar ratio of boronic ester over (1,2- or 1,3-)diol is greater than 9, preferably greater than 14, more preferably greater than 19, still more preferably greater than 49, still more preferably greater than 99, still more preferably greater than 199, still more preferably greater than 399, still more preferably greater than 499 and still more preferably greater than 999.

The person skilled in the art knows the factors involved in the position of this equilibrium. Among these factors, one can list the pH, the nature of the groups $R_1$ and $R_3$ linked to the boron atom of the boronic ester functions, the nature of the groups $R_2$, $R_2'$, $R_2''$ and $R_4$, $R_4'$, $R_4''$ present on the carbon atoms of the boronic ester functions, the concentration of water, the presence of dehydrating agents and the concentration of boronic acid (4).

The boronic esters carry a radical $R_1$ (or $R_3$) on the boron atom of the dioxaborolane or dioxaborinane ring and a radical $R_2$ and/or $R_2'$ and/or $R_2''$ (or $R_4$ and/or $R_4'$ and/or $R_4''$) on at least one of the carbon atoms of the dioxaborolane or dioxaborinane ring. In this way, compared to the diol functions, which only carry a radical on at least one of the carbon atoms of the diol function and none on the oxygen atoms, the dioxaborolane or dioxaborinane rings of the boronic esters enable two fragments/radicals of interest to be connected within the same molecule. For the same reasons, several dioxaborolane or dioxaborinane rings can be incorporated within the same molecule so as to link more than two fragments/radicals. This property is primordial for the conception and discovery of novel bioactive substances whose structures are complex. These molecules typically comprise chiral centres and various chemical functions. It is therefore primordial to be able to connect these various group within the same molecule while varying their position or their configuration.

Furthermore, under the same conditions of temperature, solvent and concentration, the boronic ester functions are compatible with a large number of chemical functions with which diol functions could give parasite reactions. Examples include acyl chloride, acyl bromide, isocyanate, thioisocyanate, acrylate, methacrylate, carboxylic acid or ester functions.

The boronic ester metathesis reaction also offers practical advantages compared to boronic ester exchange reactions resulting from successive reactions of dissociation to diols and boronic acids then recombination to boronic esters. Surprisingly, it has been discovered that boronic esters can exchange by a metathesis reaction at ambient temperature, with or without catalyst. This is a net advantage compared to boronic ester exchange reactions proceeding by dissociation and recombination of the dioxaborolane or dioxaborinane functions in that it is not necessary to add water to break the boronic ester bonds (necessary for dissociation) nor to eliminate water later to reform the dioxaborolane or dioxaborinane rings (necessary for recombination). The elimination of molecules of water in the recombination step requires either carrying out a distillation (at high temperature and/or under vacuum) or adding a dehydrating agent that has to be removed from the reaction medium later, generally by filtration. This way, the metathesis reaction greatly simplifies the process of exchange of boronic ester functions. Furthermore, metathesis enables the use of a diol intermediate to be avoided: reactivity of diols towards certain functional groups, such as acyl chloride, acyl bromide, isocyanate, thioisocyanate, acrylate, methacrylate, carboxylic acid or ester functions, can lead to parasite reactions. During the recombination reaction between diols and boronic acids (recombination reaction), byproducts such as boroxines can be formed. Boroxines are heterocycles comprising three boron atoms and three oxygen atoms alternating to form a ring of 6 heteroatoms. Boroxine rings are obtained by a condensation reaction of three molecules of boronic acid. Boroxines are in equilibrium with the corresponding boronic acids and this equilibrium is shifted toward the boroxine form by elimination of water. Therefore it is difficult to avoid the formation of this byproduct during the recombination reaction between diols and boronic acid.

As is shown in the examples, the compounds synthesised result from a metathesis reaction of the boronic esters and not from a dissociation and recombination reaction. Preferably, the presence of diols is not detected during the reaction. Then preferably, the metathesis reaction is carried out in the absence of detectable diol.

"Absence of detectable diols" designates that the analysis of reaction media by proton NMR and/or by gas chromatography and/or by infrared spectroscopy does not enable the presence of 1,2- or 1,3-diol functions to be observed in the reaction medium.

The boronic ester metathesis reaction can also occur in the presence of 1,2-diols or 1,3-diols, in particular for quantities of diols less than a mole fraction of 25% compared to the total amount of boronic ester functions, preferably less than a mole fraction of 15% compared to the total amount of boronic ester functions, more preferably less than a mole fraction of 10% compared to the total amount of boronic ester functions, still more preferably less than a mole fraction of 5% compared to the total amount of boronic ester functions, still more preferably less than a mole fraction of 2.5% compared to the total amount of boronic ester functions, still more preferably less than a mole fraction of 1% compared to the total amount of boronic ester functions, still more preferably less than a mole fraction of 0.5% compared to the total amount of boronic ester functions, still more preferably less than a mole fraction of 0.25% compared to the total amount of boronic ester functions, still more preferably less than a mole fraction of 0.1% compared to the total amount of boronic ester functions.

In a variant of the invention, the reaction is carried out in a basically anhydrous medium. "Basically anhydrous medium" designates a medium in which the hydrolysis reaction of the starting compounds, at ambient temperature (i.e. between 20° C. and 40° C.) is such that, after 12 h, the concentration of diols is less than a mole fraction of 2% compared to the total starting concentration of boronic ester functions, preferably less than a mole fraction of 1% compared to the total starting concentration of boronic ester functions, more preferably less than a mole fraction of 0.5% compared to the total starting concentration of boronic ester functions, still more preferably less than a mole fraction of 0.25% compared to the total starting concentration of boronic ester functions, still more preferably less than a mole fraction of 0.1% compared to the total starting concentration of boronic ester functions.

According to a first embodiment, the starting compounds are:
- assemblies of amino acids, in particular peptides or polypeptides, or proteins, said assemblies being linked together through boronic ester functions and, if applicable, small organic molecules containing at least one, preferably at least two, boronic ester function(s);
- Chains of amino acids, in particular peptides, polypeptides or proteins, comprising a dioxaborolane or dioxaborinane function at one, preferably at two, end(s) of their chain and, if applicable, small organic molecules containing at least one, preferably at least two, boronic ester function(s);

Such compounds can be prepared following the processes known to the person skilled in the art (4). Such compounds can notably be prepared by sequential peptide coupling, notably on solid support. Non-limiting examples include the coupling of amino acids, in particularly of peptides or polypeptides or proteins, with boronic ester, 1,2- or 1,3-diol or boronic acid groups. Among the reactions that can be used for the coupling, non-limiting examples include esterification, amidification, condensation, Michael addition, cycloaddition, nucleophilic addition to an isocyanate, ring opening reactions, coupling of thiol functions to form a disulfide function and nucleophilic substitution. And in this way may be separated by the processes known to the person skilled in the art, among which non-limiting examples include chromatography, electrophoresis or crystallisation.

According to another embodiment, the starting compounds are small organic molecules.

Step (ii.) is preferably carried out in an anhydrous solvent, in particular chosen from among alkanes, aromatic solvents, heterocycles, ethers, esters, ketones, amides, apolar aprotic solvents, halogenated solvents, heteroaromatic solvents, hydrocarbons, mineral oils, natural oils, synthetic oils, and the mixture of two or more of these solvents.

The alkanes may be linear alkanes or cycloalkanes.

Representative but non-limiting examples of linear alkanes are pentane, hexane, heptane and dodecane.

Representative but non-limiting examples of cycloalkanes are cyclohexane and cyclopentane.

Representative but non-limiting examples of aromatic solvents are benzene, toluene, xylene and anisole.

Representative but non-limiting examples of heterocycles are tetrahydrofuran and 1,4-dioxane.

Representative but non-limiting examples of ethers are diethyl ether and diisopropyl ether.

Representative but non-limiting examples of esters are ethyl acetate, methyl acetate and butyl acetate.

Representative but non-limiting examples of ketones are acetone and butanone.

Representative but non-limiting examples of amides are N,N-dimethylformamide, N,N-dimethylacetamide and N,N-diethylacetamide.

Representative but non-limiting examples of apolar aprotic solvents are acetonitrile and dimethyl sulfoxide.

Representative but non-limiting examples of halogenated solvents are dichloromethane, chloroform, carbon tetrachloride, dichloroethane and tetrachloroethylene.

Representative but non-limiting examples of halogenated aromatic solvents are chlorobenzene and trichlorobenzene.

Representative but non-limiting examples of heteroaromatic solvents are pyridine and pyrimidine.

Step (ii.) can also be performed in bulk, i.e. in the absence of solvents.

Reaction can be carried out in the presence or not of a catalyst.

Non-limiting examples of catalysts include carboxylic acids and tertiary amines.

Preferably step (ii.) is carried out in the absence of catalyst.

Step (ii.) is preferably carried out at a temperature between 0° C. and 60° C., more preferably at ambient temperature, i.e. between 20° C. and 40° C.

Step (ii.) can also be carried out at a temperature between 0° C. and 200° C., more preferably between 0° C. and 180° C.

In this way, step (ii.) can be easily carried out at the industrial scale without operating conditions that are difficult to control or potentially dangerous. For example, step (ii.) is carried out at atmospheric pressure; step (ii.) is carried out under ambient atmosphere.

The kinetics of the boronic ester metathesis reaction may be controlled by the choice of the radicals carried by the boron atom and the radicals carried by the carbon atoms of the dioxaborolane or dioxaborinane ring, by the size of the boronic ester ring, dioxaborolane ring versus dioxaborinane ring, and by the temperature, the polarity of the reaction medium and the presence of catalyst(s).

The kinetics of the boronic ester metathesis reaction can notably be adjusted by introducing electron-withdrawing or electron-donating groups on the radicals carried by the boron atom and/or by the carbon atoms of the dioxaborolane or dioxaborinane ring.

The kinetics of the metathesis reaction can notably be adjusted by varying the size and number of radicals carried by the boron atom and/or by the carbon atoms of the dioxaborolane or dioxaborinane ring.

The kinetics of the metathesis reaction can notably be adjusted by varying the number of carbon atoms present in the ring of the boronic ester function, that is by changing from a dioxaborolane ring to a dioxaborinane ring.

The kinetics of the metathesis reaction can notably be adjusted by varying the polarity of the reaction medium.

The kinetics of metathesis reaction can notably be adjusted by introducing a catalyst, such as carboxylic acids or tertiary amines.

Starting Compounds

The process of the invention can be applied to a very large number of compounds, provided that:
- the boron of the dioxaborolane or dioxaborinane ring is directly linked to a carbon atom of a hydrocarbon radical;
- at least one carbon atom of the dioxaborolane or dioxaborinane ring is monosubstituted, the other carbon atoms of the dioxaborolane or dioxaborinane ring being non-substituted or monosubstituted.

The compounds are chosen as a function of the desired activity and the final use of the library.

In particular, it may be of interest that at least one of the compounds comprises a centre of asymmetry. In particular, the compound may be a chiral compound.

The dioxaborinane rings are more stable to hydrolysis. In this way, compounds comprising dioxaborinane rings may be preferred when the reaction medium contains traces of water.

All other parameters being equal, the metathesis of dioxaborolane rings is faster than the metathesis of dioxaborinane rings. In this way, compounds comprising dioxaborolane rings may be preferred when it is desired to reduce the time necessary to generate the libraries.

The compounds may for example be:
- assemblies of amino acids, in particular peptides or polypeptides, or proteins, said assemblies being linked together through boronic ester functions and, if applicable, small organic molecules containing at least one, preferably at least two, boronic ester function(s);
- Chains of amino acids, in particular peptides, polypeptides or proteins, comprising a dioxaborolane or dioxaborinane function at one, preferably at two, end(s) of their chain and, if applicable, small organic molecules containing at least one, preferably at least two, boronic ester function(s);

The assemblies of amino acids are relatively stable to hydrolysis.

The compounds may for example be small organic molecules.

The dioxaborolane groups are preferably prepared from 1,2-diols and the dioxaborinane groups are preferably prepared from 1,3-diols.

Without wishing to be limitative, the compounds are preferably of formula (Ia) or (Ib), as described previously, in which:

$R_1$, $R_2$, $R_2'$, $R_2''$, $R_3$, $R_4$, $R_4'$ and $R_4''$ are independently chosen from among alkyl, alkenyl, alkynyl, halogenoalkyl, heteroalkyl, cycloalkyl, polycycloalkyl, cycloheteroalkyl, polycycloheteroalkyl, aryl, cycloheteroaryl, polyaryl, polycycloheteroaryl, aralkyl or alkyl-aryl radicals; each of these radicals may be substituted with one or more radicals, preferably chosen from among halogens, —OH, —NH$_2$, —NHRz, —NRzR'z, —C(O)—H, —C(O)—Rz, —C(O)—OH, —C(O)—O—Rz, —O—C(O)—Rz, —O—C(O)—O—Rz, —O—C(O)—N(H)—Rz, —N(H)—C(O)—O—Rz, —O—Rz, —SH, —S—Rz, —S—S—Rz, —CO—NH$_2$, —C(O)—N(H)—Rz, —C(O)—NRzR'z, —N(H)—C(O)—Rz, —N(Rz)-C(O)—Rz', —CN, —NCO, —NCS, boronic esters, alkyls, alkenyls, alkynyls, halogenoalkyls, cycloalkyls, polycycloalkyls, cycloheteroalkyls, polycycloheteroalkyls, aryls, cycloheteroaryls, polyaryls, polycycloheteroaryles, aralkyls or alkyl-aryls, heteroaralkyls, with Rz and R'z, identical or different, representing a hydrocarbon radical, in particular with Rz and R'z, identical or different, representing a $C_1$-$C_{50}$ alkyl, $C_2$-$C_{50}$ alkenyl, $C_2$-$C_{50}$ alkynyl, $C_1$-$C_{50}$ halogenoalkyl or $C_1$-$C_{50}$ heteroalkyl radical.

A —O—CO—Rz radical may in particular be a —O—CO—CH=CH$_2$ or —O—CO—C(CH$_3$)=CH$_2$ radical.

An alkyl-aryl radical may in particular be a -Ph-CH=CH$_2$ radical.

The boronic ester is preferably a dioxaborolane or dioxaborinane ring in which:
- the boron of the dioxaborolane or dioxaborinane ring is directly linked to a carbon atom of a hydrocarbon radical;
- at least one carbon atom of the dioxaborolane or dioxaborinane ring is monosubstituted, the other carbon atoms of the dioxaborolane or dioxaborinane ring being non-substituted or monosubstituted.

Preferably, $R_1$, $R_2$, $R_2'$, $R_2''$, $R_3$, $R_4$, $R_4'$ and $R_4''$ do not comprise a 1,2-diol or 1,3-diol function.

Preferably, only one of the carbons of the dioxaborolane or dioxaborinane ring carries a substituent comprising more than 10 carbon atoms. In particular, when $R_2$, $R_2'$ or $R_2''$ (or $R_4$, $R_4'$ or $R_4''$) represents a radical with more than 6 carbon atoms, the other radicals $R_2$, $R_2'$, $R_2''$ (or $R_4$, $R_4'$, $R_4''$) comprise fewer than 6 carbon atoms.

In a particular embodiment, $R_2$, $R_2'$, $R_2''$, $R_4$, $R_4'$ and $R_4''$ are chosen from among H or an alkyl, alkenyl, alkynyl or halogenoalkyl radical.

In a particular embodiment, two of $R_2$, $R_2'$ and $R_2''$, or two of $R_4$, $R_4'$ and $R_4''$, together form an aliphatic or aromatic ring.

In one embodiment, n=0 and one of $R_2$ or $R_2'$ represents H.

In one embodiment, m=0 and one of $R_4$ or $R_4'$ represents H.

Process

The process preferably comprises, following the preparation of a compound library according to the invention, an evaluation step of the activity of the compounds in the library. This may be the evaluation of the chemical, biological, therapeutic, biochemical or physicochemical activity of the compounds in the library.

This step may be carried out by any means known to the person skilled in the art.

Prior to this evaluation step of the activity of the compounds in the library, the process may comprise, or not, a separation step of compounds in the library. Preferably, the evaluation step of the activity of the compounds and library is carried out without prior separation of the compounds in the library.

Another object of the invention is a compound library comprising more than two different compounds, each comprising at least one dioxaborolane or dioxaborinane ring. In said compounds:
- the boron of the dioxaborolane or dioxaborinane group is directly linked to a carbon atom of a hydrocarbon radical;
- at least one carbon atom of the dioxaborolane or dioxaborinane ring is monosubstituted, the other carbon atoms of the dioxaborolane or dioxaborinane ring being non-substituted or monosubstituted;
- in at least two compounds, the hydrocarbon radicals linked to the boron are different;
- in at least two compounds, the substituents carried by at least one of the carbon atoms of the dioxaborolane or dioxaborinane rings are different and/or the size of the boronic ester ring is different.

EXAMPLES

The following examples illustrate the synthesis and the characterization of boronic ester compounds.

Example 1: General Procedure for the Synthesis of Boronic Esters, NMR Characterizations

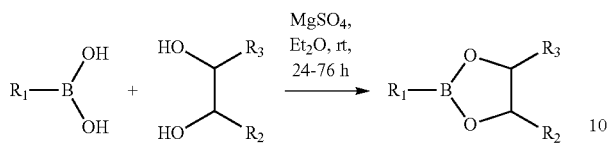

The boronic acid (1 eq.) and the diol (1.01 eq.) are mixed in diethyl ether (ca. 3 mL/1 mmol of the boronic acid). After five minutes, water (0.1 mL/3 mL Et$_2$O) is added. After complete dissolution of all reactants magnesium sulfate (0.5 g/3 mL Et$_2$O) is added gradually and the reaction mixture is stirred at room temperature for 24-76 hours. Then, the reaction mixture is filtered and concentrated under reduced pressure. The obtained product is introduced in heptane and the mixture is stirred at room temperature for ten minutes, filtered and concentrated under reduced pressure to yield the boronic ester as a white solid or transparent oil.

3,5-Dimethylphenylboronic acid 1,2-propanediol ester: MR 02-066

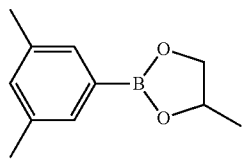

$^1$H NMR (CDCl$_3$, 400 MHz): δ 7.46 (s, 2H), 7.13 (s, 1H), 4.73 (m, 1H), 4.46 (dd, J=8.8 Hz, 1.2 Hz, 1H), 3.90 (dd, J=8.8 Hz, 1.2 Hz, 1H), 2.34 (s, 6H), 1.43 (d, J=6.0 Hz, 3H).

$^{13}$C NMR (CDCl$_3$, 100 MHz): δ 137.2, 133.2, 132.5, 73.72, 72.5, 21.8, 21.2.

MS: (100%) m/z: [M] Calculated for C11H15BO2 190.1165. found 190.07.

3,5-Dimethylphenylboronic acid 1,2-octanediol ester: MR 02-067

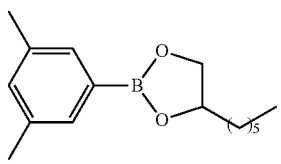

$^1$H NMR (CDCl$_3$, 400 MHz): δ 7.43 (s, 2H), 7.12 (s, 1H), 4.56 (m, 1H), 4.41 (dd, J=8.8 Hz, 1.2 Hz), 3.94 (dd, J=8.8 Hz, 1.2 Hz, 1H), 2.33 (s, 6H), 1.76-1.27 (m, 10H), 0.89 (t, J=6.8 Hz, 3H).

$^{13}$C NMR (CDCl$_3$, 100 MHz): δ 137.2, 133.0, 132.5, 77.5, 71.0, 36.2, 31.9, 28.9, 25.1, 22.5, 21.2, 14.0.

3,5-Dimethylphenylboronic acid 1,2-dodecanediol ester: MR 02-068

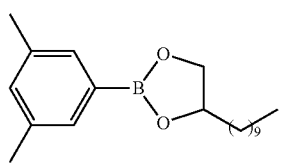

$^1$H NMR (CDCl$_3$, 400 MHz): δ 7.45 (s, 2H), 7.12 (s, 1H), 4.57 (m, 1H), 4.42 (dd, J=8.8 Hz, 1.2 Hz, 1H), 3.94 (dd, J=8.8 Hz, 1.2 Hz, 1H), 2.34 (s, 6H), 1.73-1.28 (m, 18H), 0.90 (t, J=6.8 Hz, 3H).

$^{13}$C NMR (CDCl$_3$, 100 MHz): δ 137.2, 133.1, 132.5, 77.5, 71.7, 36.2, 31.9, 29.7, 29.6, 29.5, 29.4, 24.9, 22.7, 21.2, 14.1.

3,5-Bis(trifluoromethyl)phenylboronic acid 1,2-propanediol ester: MR 02-069

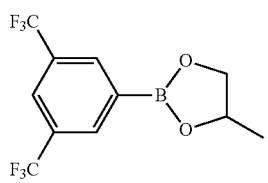 [SMILES: CC1COB(c2cc(C(F)(F)F)cc(C(F)(F)F)c2)O1]

$^1$H NMR (CDCl$_3$, 400 MHz): δ 8.24 (s, 2H), 7.96 (s, 1H), 4.79 (m, 1H), 4.54 (dd, J=8.8 Hz, 1.2 Hz, 1H), 3.95 (dd, J=8.8 Hz, 1.2 Hz, 1H), 1.46 (d, J=6.0 Hz, 3H).

$^{13}$C NMR (CDCl$_3$, 100 MHz): δ 134.7, 124.9, 124.8, 122.1, 74.3, 72.8, 21.6.

3,5-Bis(trifluoromethyl)phenylboronic acid 1,2-hexanediol ester: MR 02-070 et MR 04-007

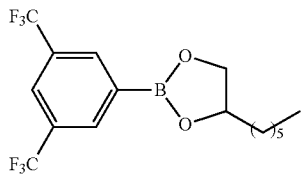

$^1$H NMR (CDCl$_3$, 400 MHz): δ 8.25 (s, 2H), 7.96 (s, 1H), 4.68-4.61 (m, 1H), 4.49 (dd, J=8.8 Hz, 1.2 Hz, 1H), 4.01 (dd, J=8.8 Hz, 1.2 Hz, 1H), 1.81-1.32 (m, 10H), 0.90 (t, J=6.8 Hz, 3H).

$^{13}$C NMR (CDCl$_3$, 100 MHz): δ 134.7, 131.1, 130.8, 124.8, 78.3, 71.6, 36.1, 31.7, 29.0, 25.0, 22.5, 13.9.

3,5-Bis(trifluoromethyl)phenylboronic acid 1,2-dodecanediol ester: MR 02-071

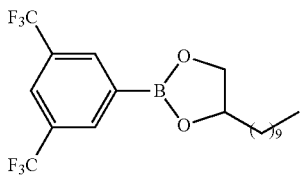

¹H NMR (CDCl₃, 400 MHz): δ 8.24 (s, 2H), 7.96 (s, 1H), 4.67-4.60 (m, 1H), 4.49 (dd, J=8.8 Hz, 1.2 Hz, 1H), 4.01 (dd, J=8.8 Hz, 1.2 Hz, 1H), 1.80-1.27 (m, 18H), 0.88 (t, J=6.8 Hz, 3H).

¹³C NMR (CDCl₃, 100 MHz): δ 134.7, 131.2, 130.8, 124.8, 78.3, 71.6, 36.1, 31.9, 29.6, 29.5, 29.4, 29.3, 29.1, 24.9, 22.7, 14.1.

3,5-Dichlorophenylboronic acid 1,2-propanediol ester: MR 02-072

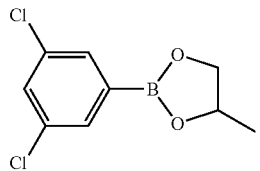

¹H NMR (CDCl₃, 400 MHz): δ 7.64 (s, 2H), 7.43 (s, 1H), 4.71 (m, 1H), 4.46 (dd, J=8.8 Hz, 1.2 Hz, 1H), 3.88 (dd, J=8.8 Hz, 1.2 Hz, 1H), 1.42 (t, J=6.8 Hz, 3H).

¹³C NMR (CDCl₃, 100 MHz): δ 134.8, 132.9, 131.2, 74.0, 72.3, 21.3.

3,5-Dichlorophenylboronic acid 1,2-hexanediol ester: MR 02-073

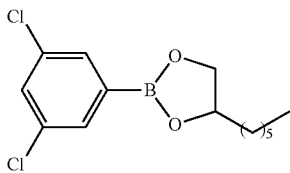

¹H NMR (CDCl₃, 400 MHz): δ 7.65 (d, J=2 Hz, 1H), 7.43 (t, J=2 Hz, 1H), 4.61-4.54 (m, 1H), 4.43 (dd, J=8.8 Hz, 1.2 Hz, 1H), 3.95 (dd, J=8.8 Hz, 1.2 Hz), 1.76-1.26 (m, 10H), 0.89 (t, J=6.8 Hz, 3H).

¹³C NMR (CDCl₃, 100 MHz): δ 134.8, 132.8, 131.2, 78.0, 71.5, 36.1, 31.7, 29.2, 25.0, 22.6, 14.1.

MS: (100%) m/z: [M] Calculated for C9H17BO2 168.1322. found [M+] 169.0.

3,5-Dichlorophenylboronic acid 1,2-dodecanediol ester: MR 02-074

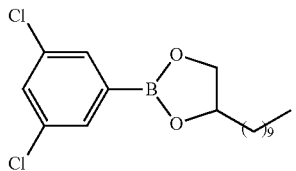

¹H NMR (CDCl₃, 400 MHz): δ 7.65 (d, J=2 Hz, 1H), 7.45 (t, J=2 Hz, 1H), 4.61-4.54 (m, 1H), 4.43 (dd, J=8.8, 1.2 Hz, 1H), 3.95 (dd, J=8.8 Hz, 1.2 Hz), 1.76-1.27 (m, 18H), 0.88 (t, J=6.8 Hz, 3H).

¹³C NMR (CDCl₃, 100 MHz): δ 134.8, 132.8, 131.2, 78.1, 71.5, 36.1, 31.9, 29.6, 29.5, 29.4, 29.3, 29.2, 24.9, 22.7, 14.1.

MS: (100%) m/z: [M] Calculated for C15H31BO2 254.2417. found [M] 254.05.

Phenylboronic acid pinacol ester: MR 03-072

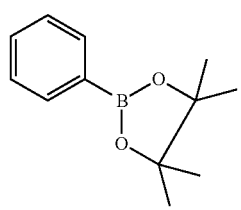

¹H NMR (CDCl₃, 400 MHz): δ 7.85 (m, 2H), 7.45 (m, 3H), 1.38 (s, 12H).

¹³C NMR (CDCl₃, 100 MHz): δ 134.8, 131.2, 127.8, 83.7, 25.0.

Cyclohexylboronic acid 1,2-propanediol ester: MR 03-073

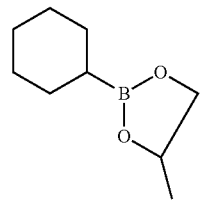

¹H NMR (CDCl₃, 400 MHz): δ 4.48 (m, 1H), 4.23 (m, 1H), 3.66 (m, 1H), 1.69-1.01 (m, 14H).

¹³C NMR (CDCl₃, 100 MHz): δ 73.0, 72.0, 28.1, 27.2, 26.7, 21.6.

Propylboronic acid 1,2-dodecanediol ester: MR 03-074

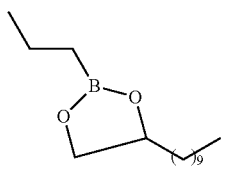

<sup>1</sup>H NMR (CDCl<sub>3</sub>, 400 MHz): δ 4.34 (m, 1H), 4.21 (m, 1H), 3.74 (m, 1H), 1.68-1.25 (m, 22H), 0.95-0.79 (m, 6H).
<sup>13</sup>C NMR (CDCl<sub>3</sub>, 100 MHz): δ 76.8, 70.7, 36.2, 32.0, 29.6, 29.6, 29.5, 29.3, 25.0, 22.6, 17.5, 16.9, 14.0.

3,5-Bis(trifluoromethyl)phenylboronic acid pyrocatechol ester: MR 03-079

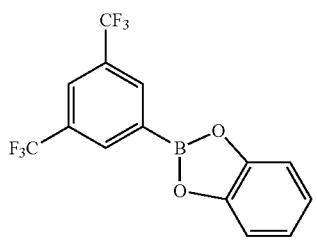 [SMILES: FC(F)(F)c1cc(B2Oc3ccccc3O2)cc(C(F)(F)F)c1]

<sup>1</sup>H NMR (CDCl<sub>3</sub>, 400 MHz): δ 8.52 (s, 2H), 8.01 (s, 1H), 7.38 (m, 2H), 7.19 (m, 2H).
<sup>13</sup>C NMR (CDCl<sub>3</sub>, 100 MHz): δ 148.0, 134.8, 125.8, 124.4, 123.5, 121.9, 113.0.
MS: (100%) m/z: [M] Calculated for C14H7BF6O2 332.0443. found [M] 332.03.

Cyclohexylboronic acid 1,2-propanediol ester: MR 03-081

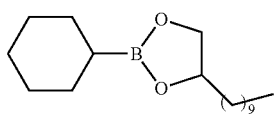

<sup>1</sup>H NMR (CDCl<sub>3</sub>, 400 MHz): δ 4.32 (m, 1H), 4.18 (t, J=8.4 Hz, 1H), 3.71 (t, J=8.4 Hz, 1H), 1.87-0.98 (m, 29H), 0.85 (t, J=6.8 Hz, 3H).
<sup>13</sup>C NMR (CDCl<sub>3</sub>, 100 MHz): δ 76.7, 70.5, 65.8, 36.2, 31.9, 29.6, 29.5, 29.3, 28.0, 27.1, 26.7, 24.9, 22.7, 14.1.

Propylboronic acid 1,2-propanediol ester: MR 03-082

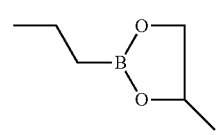

<sup>1</sup>H NMR (CDCl<sub>3</sub>, 400 MHz): δ 4.48 (m, 1H), 4.22 (t, J=8.4 Hz, 1H), 3.66 (t, J=8.4 Hz, 1H), 1.47-1.16 (m, 4H), 0.91 (t, J=7.2 Hz, 3H), 0.79 (t, J=7.2 Hz, 3H).
<sup>13</sup>C NMR (CDCl<sub>3</sub>, 100 MHz): δ 72.9, 72.0, 21.9, 17.5, 16.8.

3,5-Dichlorophenylboronic acid pyrocatechol ester: MR 04-006

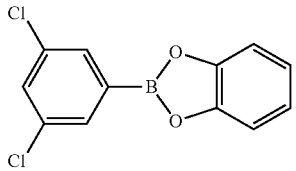 [SMILES: Clc1cc(Cl)cc(B2Oc3ccccc3O2)c1]

<sup>1</sup>H NMR (CDCl<sub>3</sub>, 400 MHz): δ 7.93 (s, 2H), 7.56 (s, 1H), 7.33 (m, 2H), 7.16 (m, 2H).
<sup>13</sup>C NMR (CDCl<sub>3</sub>, 100 MHz): δ 143.4, 132.9, 132.3, 123.3, 121.4, 115.3, 112.9.

3,5-Dimethylphenylboronic acid 1,3-butanediol ester: MR 04-012

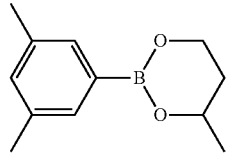

<sup>1</sup>H NMR (CDCl<sub>3</sub>, 400 MHz): δ 7.41 (s, 2H), 7.05 (s, 1H), 4.28 (m, 1H), 4.19 (m, 1H), 4.10 (m, 1H), 2.3 (s, 6H), 2.02 (m, 1H), 1.81 (m, 1H), 1.37 (d, J=6.4 Hz, 3H).
<sup>13</sup>C NMR (CDCl<sub>3</sub>, 100 MHz): δ136.8, 132.2, 131.3, 67.6, 61.1, 34.3, 22.9, 21.3.
MS: (100%) m/z: [M] Calculated pour C<sub>12</sub>H<sub>17</sub>BO<sub>2</sub> 204.1322. found [M] 204.10.

4-Fluorophenylboronic acid 1,2-dodecanediol ester: MR X-002

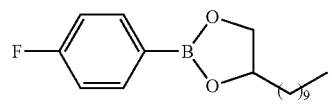

<sup>1</sup>H NMR (CDCl<sub>3</sub>, 400 MHz): δ 7.83 (d, 2H, J=6.4, 8.8 Hz), 7.08 (dd, 2H, J=8.8, 8.8 Hz), 4.58 (ddt, 1H, J=5.6, 7.2, 7.2 Hz), 4.44 (dd, 1H, J=8.0, 8.8 Hz), 3.96 (dd, 1H, J=7.2, 8.8 Hz), 1.27-1.80 (m, 18H), 0.91 (t, 3H J=7.2 Hz).
<sup>13</sup>C NMR (CDCl<sub>3</sub>, 100 MHz): δ 164.2, 137.1, 115.0, 77.7, 71.3, 36.2, 31.9, 29.6, 29.6, 29.6, 29.5, 29.4, 25.0, 22.7, 14.1.

4-Fluorophenylboronic acid 1,2-propanediol ester: MR X-010

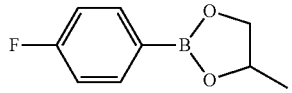

¹H NMR (CDCl₃, 400 MHz): δ 7.82 (dd, 2H, J=6.2, 8.7 Hz), 7.05 (CDCl₃, 400 MHz): δ 7.82 (dd 2H, J=6.2, 8.7 Hz), 7.05 (dd 2H, J=8.7, 8.8 Hz), 4.72 (ddt, 1H, J=6.4, 7.2, 8.8 Hz), 4.45 (dd, 1H, J=7.8, 8.8 Hz), 3.88 (dd, 1H, J=7.2, 8.8 Hz), 1.41 (d, 3H J=6.0 Hz).
¹³C NMR (CDCl₃, 100 MHz): δ 165.16 (d, 1JCF=249.5 Hz), 137.1 (CH, d 3JCF=8.0 Hz), 115.0 (CH, d, 2JCF=20.1 Hz), 73.9 (CH2), 72.6 (CH), 21.8 (CH3).

Cyclohexylboronic acid 1,3-butanediol ester: MR 04-014

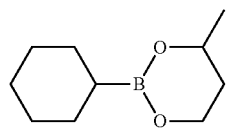

¹H NMR (CDCl₃, 400 MHz): δ 4.17-3.87 (m, 3H), 1.98-1.49 (m, 7H), 1.37-1.14 (m, 8H), 0.78 (t, J=8.8 Hz, 1H).
¹³C NMR (CDCl₃, 100 MHz): δ 67.0, 61.8, 60.9, 28.2, 27.4, 26.9, 23.0.

Phenylboronic acid 1,2-propanediol ester: MR 05-026

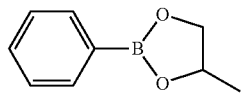

¹H NMR (CDCl₃, 400 MHz): δ 7.84 (d, J=5.6 Hz, 2H), 7.52-7.38 (m, 3H), 4.78-4.68 (m, 1H), 4.64 (dd, J=1.2 Hz, 8.8 Hz, 1H), 3.90 (dd, J=1.6 Hz, 8.8 Hz, 1H), 1.43 (d, J=6.4 Hz, 3H).
¹³C NMR (CDCl₃, 100 MHz): δ 134.7, 131.5, 127.9, 73.7, 72.4, 21.8.

Phenylboronic acid 1,2-butananediol ester: MR 2016a

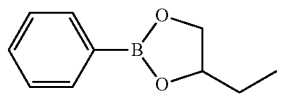

¹H NMR (CDCl₃, 400 MHz): δ 7.84 (d, J=6.4 Hz, 2H), 7.51-7.48 (m, 3H), 4.55 (m, 1H), 4.43 (dd, J=1.2 Hz, 8.8 Hz, 1H), 3.98 (dd, J=2 Hz, 8.8 Hz, 1H), 1.82-1.63 (m, 2H), 1.04 (t, J=7.6 Hz, 3H).

¹³C NMR (CDCl₃, 100 MHz): δ 134.9, 131.4, 127.8, 78.6, 70.8, 29.0, 9.0.

3,5-Dimethylphenylboronic acid 1,2-butanediol ester: MR 2016b

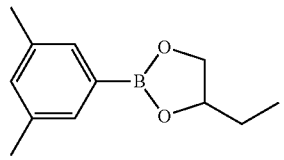

¹H NMR (CDCl₃, 400 MHz): δ 7.45 (s, 2H), 7.12 (s, 1H), 4.94-4.56 (m, 1H), 4.42 (dd, J=0.8 Hz, 8.8 Hz, 1H), 3.96 (dd, J=2.0 Hz, 8.8 Hz, 1H), 2.35 (s, 6H), 1.80-1.62 (m, 2H), 1.02 (t, J=7.6 Hz, 3H).
¹³C NMR (CDCl₃, 100 MHz): δ 137.4, 133.2, 132.9, 78.5, 70.7, 28.8, 20.9, 8.7.

Phenylboronic acid 1,3-butanediol ester: MR 05-033

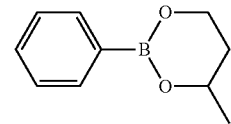

¹H NMR (CDCl₃, 400 MHz): δ 7.83 (d, J=8.0 Hz, 2H), 7.48-7.35 (m, 3H), 4.35-4.10 (m, 3H), 2.04-1.97 (m, 1H), 1.84-1.76 (m, 1H), 1.40 (d, J=6.4 Hz, 3H).
¹³C NMR (CDCl₃, 100 MHz): δ 133.7, 130.4, 127.6, 67.3, 61.4, 34.2, 23.0.

Example 2: Metathesis Reaction Between Boronic Esters

The following examples illustrate the preparation of libraries of compounds by boronic ester metathesis and illustrate for example the influence of the substituents linked to the atoms of dioxaborolane or dioxaborinane rings, the size of boronic ester rings, the temperature, the polarity of the reaction medium, the presence of catalysts of boronic ester metathesis.

A solution of a boronic ester MR-X (0.1 mmol per g of solvent) in the anhydrous solvent chosen for the reaction and a solution of a boronic ester MR-Y (0.1 mmol per g of solvent) in the anhydrous solvent chosen for the reaction are mixed. The resulting solution is stirred at a fixed temperature and the evolution of the concentration of the different components of the mixture is monitored regularly by gas chromatography.

2.1 Metathesis Between Phenylboronic Esters

The examples were conducted in three solvents at 5° C.: anhydrous hexane, anhydrous chloroform and anhydrous tetrahydrofuran.

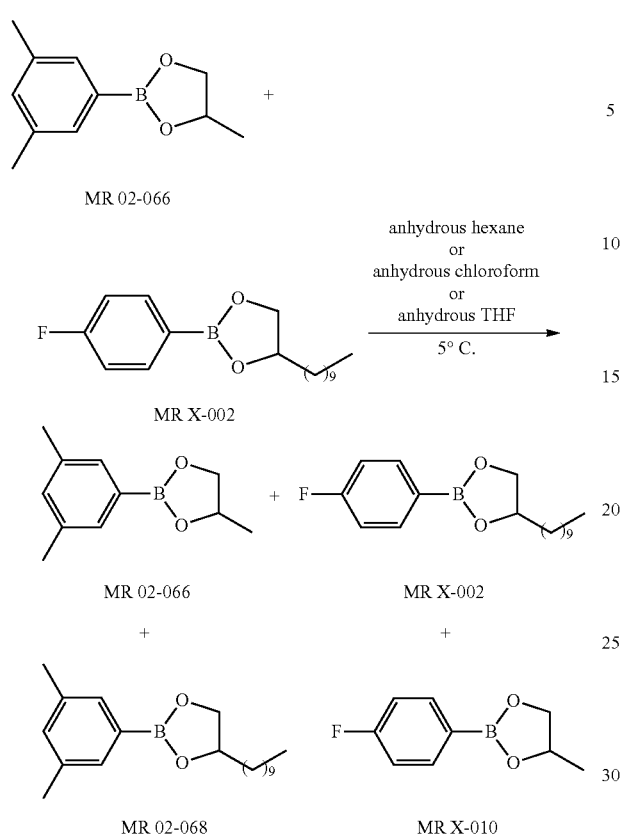

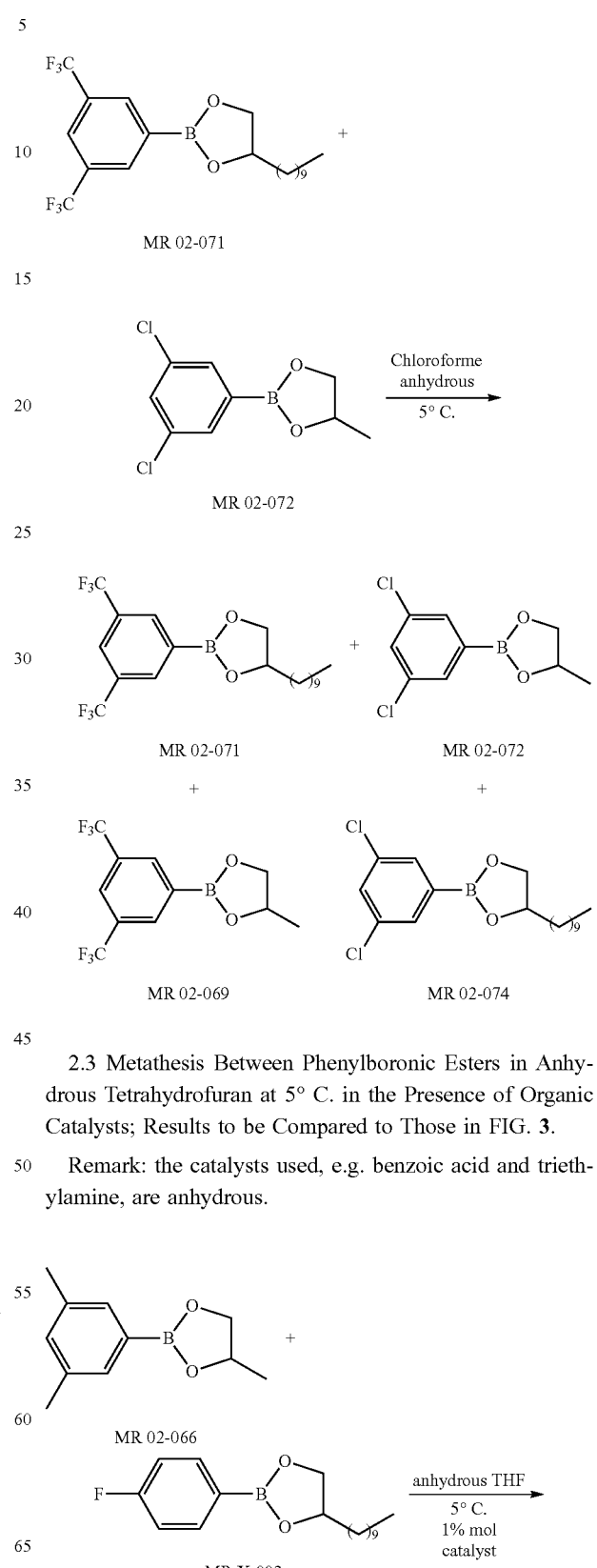

The evolution of the molar percentage (ordinate; without unit) of the different boronic esters in time (abscissa; minutes) during the metathesis between the two phenylboronic esters in anhydrous hexane at 5° C. is displayed in FIG. 1. It is observed that after 50 minutes the mixture contains equimolar quantities of the compounds MR 02-066, MR X-002, MR 02-068, MR X-010.

Figure 2:
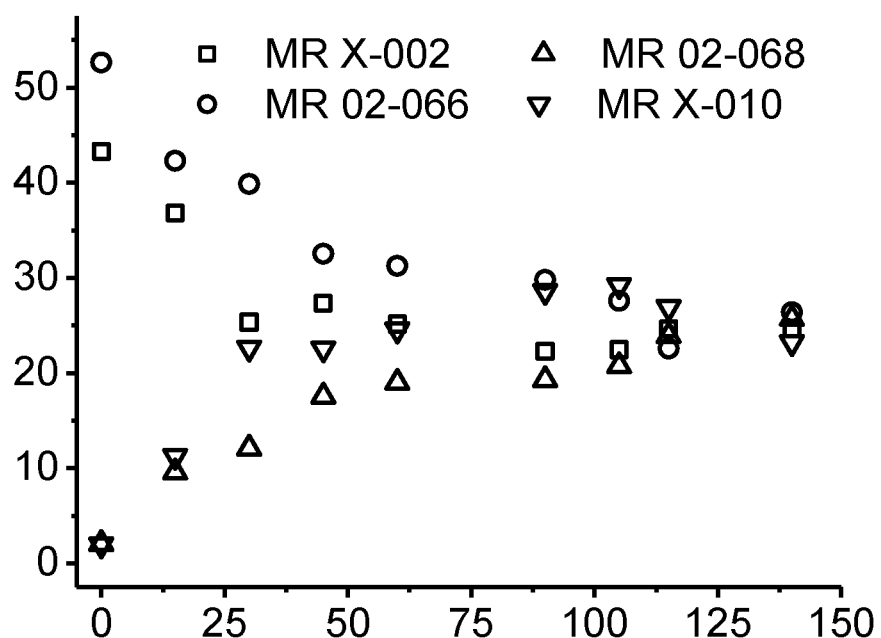
FIG. 2. Evolution of the molar percentage (ordinate; without unit) of the different boronic esters as a function of time (abscissa; minutes) during the metathesis of two phenylboronic esters in anhydrous chloroform at 5° C.

The evolution of the molar percentage (ordinate; without unit) of the different boronic esters in time (abscissa; minutes) during the metathesis between the two phenylboronic esters in anhydrous chloroform at 5° C. is displayed in FIG. 2. It is observed that after 120 minutes the mixture contains equimolar quantities of the compounds MR 02-066, MR X-002, MR 02-068, MR X-010.

Figure 3:
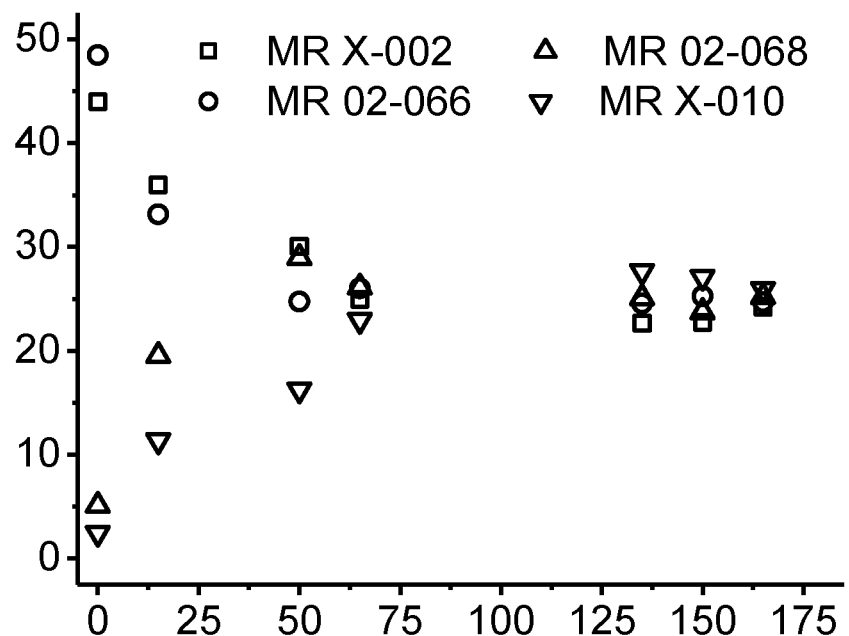
FIG. 3. Evolution of the molar percentage (ordinate; without unit) of the different boronic esters as a function of time (abscissa; minutes) during the metathesis of two phenylboronic esters in anhydrous tetrahydrofuran at 5° C.

The evolution of the molar percentage (ordinate; without unit) of the different boronic esters in time (abscissa; minutes) during the metathesis between the two phenylboronic esters in anhydrous tetrahydrofuran at 5° C. is displayed in FIG. 3. It is observed that after 175 minutes the mixture contains equimolar quantities of the compounds MR 02-066, MR X-002, MR 02-068, MR X-010.

2.2 Tests in Anhydrous Chloroform at 5° C. to Illustrate the Influence of Substituents Attached to the Aromatic Ring of Phenylboronic Esters; Results to be Compared to Those of FIG. 2.

Figure 4:
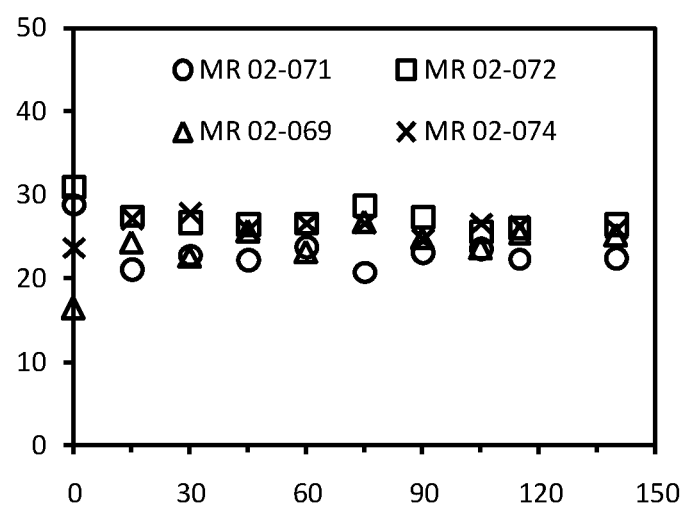
FIG. 4. Change in molar fraction (y-axis, without units) of the different boronic esters as a function of time (abscissa; minutes) during the metathesis of two phenylboronic esters in anhydrous chloroform at 5° C.

The evolution of the molar percentage (ordinate; without unit) of the different boronic esters in time (abscissa; minutes) during the metathesis between the two phenylboronic esters in anhydrous chloroform at 5° C. is displayed in FIG. 4.

2.3 Metathesis Between Phenylboronic Esters in Anhydrous Tetrahydrofuran at 5° C. in the Presence of Organic Catalysts; Results to be Compared to Those in FIG. 3.

Remark: the catalysts used, e.g. benzoic acid and triethylamine, are anhydrous.

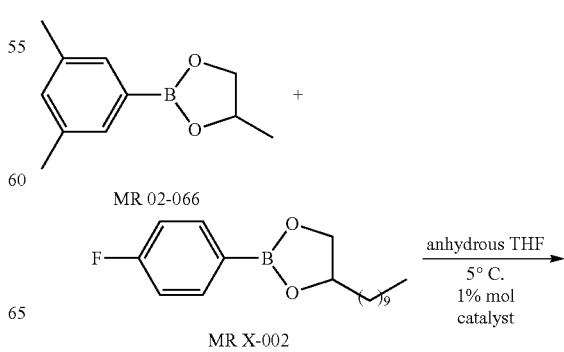

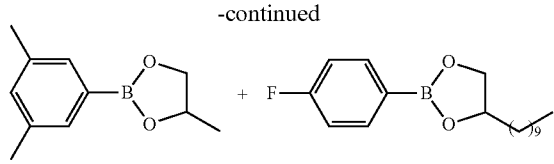

MR 02-066    MR X-002

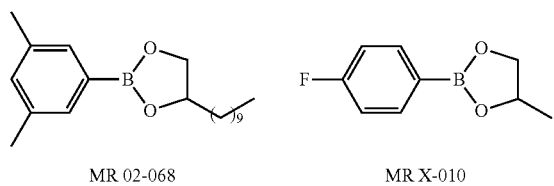

MR 02-068    MR X-010

Figure 5:
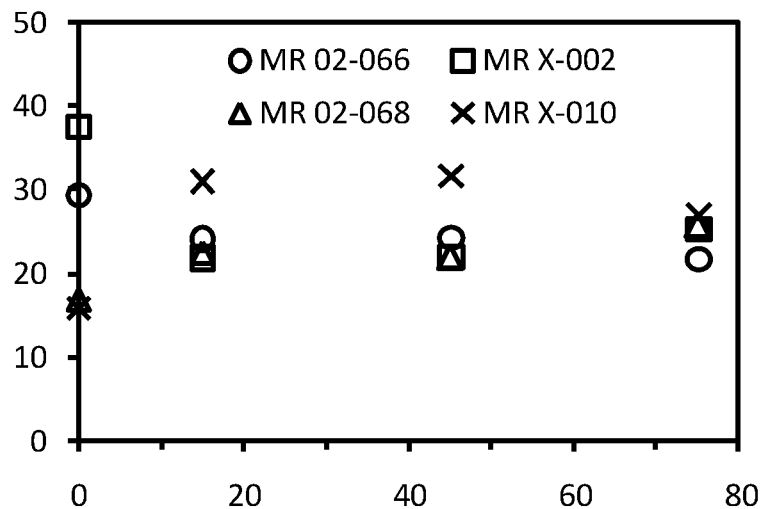
FIG. 5. Evolution of the molar percentage (ordinate; without unit) of the different boronic esters as a function of time (abscissa; minutes) during the metathesis of two phenylboronic esters in anhydrous tetrahydrofuran at 5° C. in the presence of a 1% molar fraction of anhydrous triethylamine.

The evolution of the molar percentage (ordinate; without unit) of the different boronic esters in time (abscissa; minutes) during the metathesis between the two phenylboronic esters in anhydrous tetrahydrofuran at 5° C. in the presence of 1 mol % of anhydrous triethylamine is displayed in FIG. 5.

Figure 6:
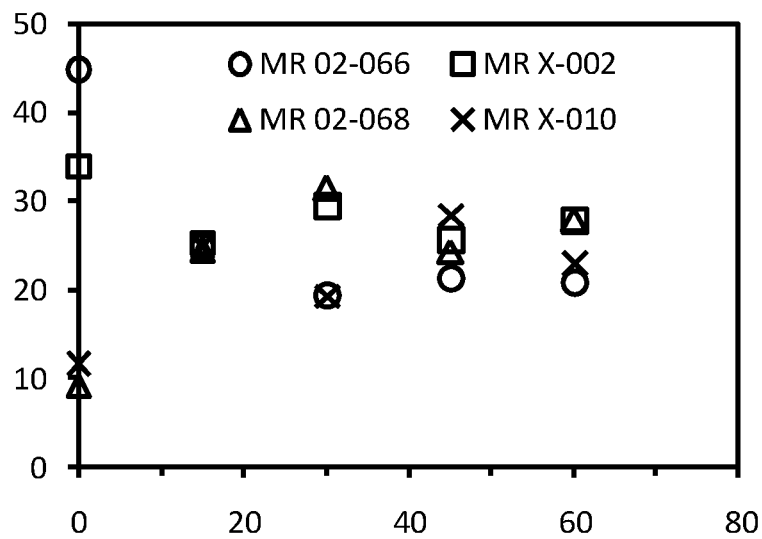
FIG. 6. Evolution of the molar percentage (ordinate; without unit) of the different boronic esters as a function of time (abscissa; minutes) during the metathesis of two phenylboronic esters in anhydrous tetrahydrofuran at 5° C. in the presence of a 1% molar fraction of anhydrous benzoic acid.

The evolution of the molar percentage (ordinate; without unit) of the different boronic esters in time (abscissa; minutes) during the metathesis between the two phenylboronic esters in anhydrous tetrahydrofuran at 5° C. in the presence of 1 mol % of anhydrous benzoic acid is displayed in FIG. 6.

2.4 Metathesis Between Alkylboronic Esters

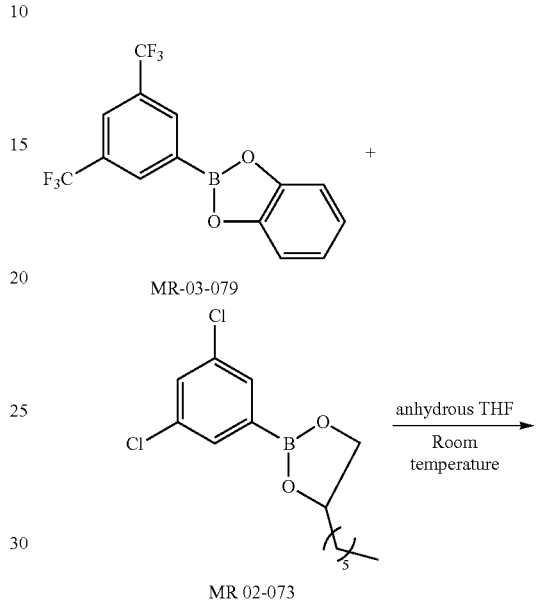

MR 03-074    MR 03-073

MR 03-074    MR 03-073

MR 03-082    MR 03-081

Figure 7:
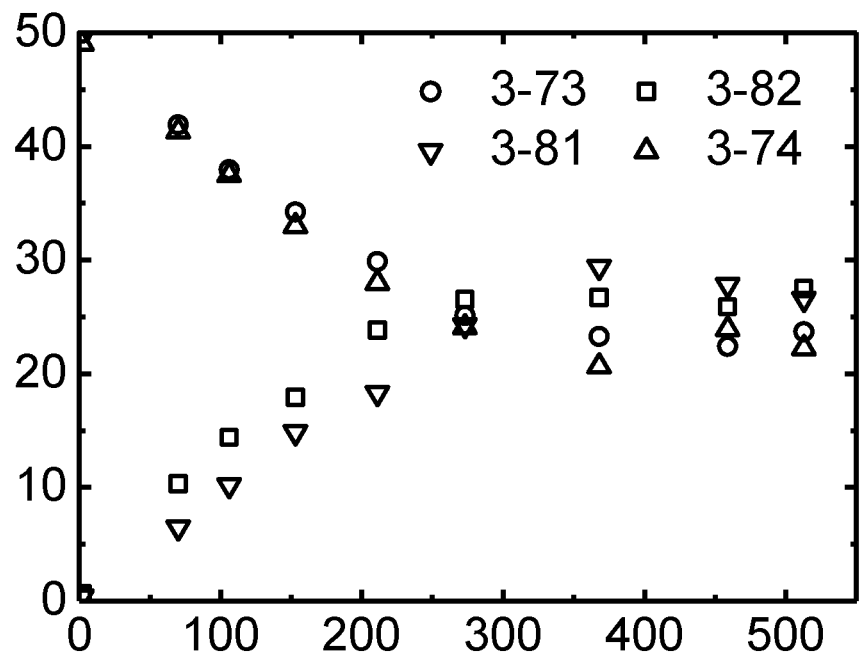
FIG. 7. Evolution of the molar percentage (ordinate; without unit) of the different boronic esters as a function of time (abscissa; minutes) during the metathesis of two alkylboronic esters in anhydrous tetrahydrofuran at room temperature FIG. 8. Evolution of the molar percentage (ordinate; without unit) of the different boronic esters as a function of time (abscissa; minutes) during the metathesis of boronic esters containing respectively an aryldiol substituent and an alkyldiol substituent in anhydrous tetrahydrofuran at room temperature FIG. 9. Evolution of the molar percentage (ordinate; without unit) of the different boronic esters as a function of time (abscissa; minutes) during the metathesis of boronic esters containing respectively a 1,2-alkyldiol substituent and a 1,3-alkyldiol substituent in anhydrous tetrahydrofuran at room temperature FIG. 10. Evolution of the molar percentage (ordinate; without unit) of the different boronic esters as a function of time (abscissa; minutes) during the synthesis of a library of 9 boronic esters in anhydrous tetrahydrofuran at room temperature FIG. 11. Evolution of the molar percentage (ordinate; without unit) as a function of time (abscissa; minutes) of the two starting boronic esters and of the two boronic esters formed during the metathesis reaction of two phenylboronic esters in bulk at 60° C.

The evolution of the molar percentage (ordinate; without unit) of the different boronic esters in time (abscissa; minutes) during the metathesis between the two alkylboronic esters in anhydrous tetrahydrofuran at room temperature is displayed in FIG. 7.

2.5 Metathesis Between Boronic Esters Containing Respectively an Aryldiol Substituent and an Alkyldiol Substituent

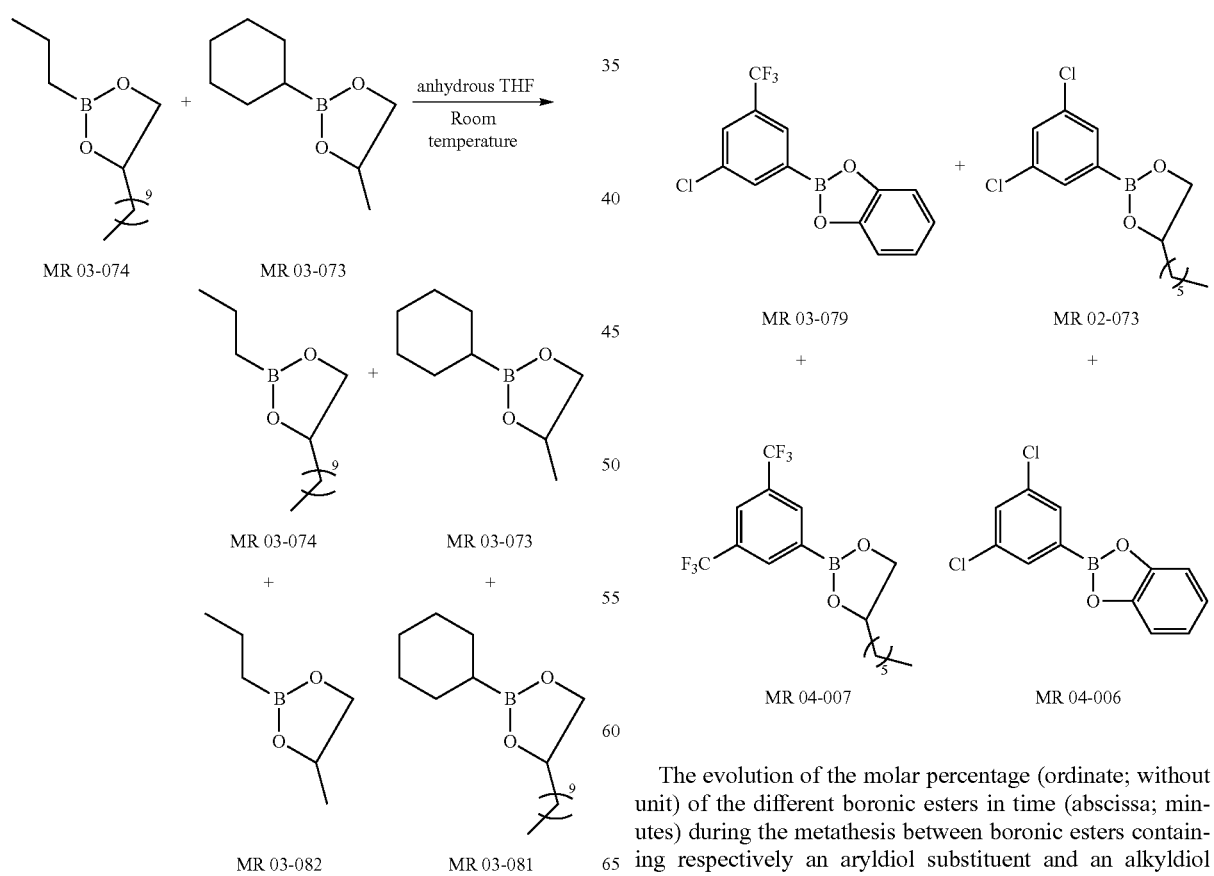

MR-03-079

MR 02-073

MR 03-079    MR 02-073

MR 04-007    MR 04-006

Figure 8:
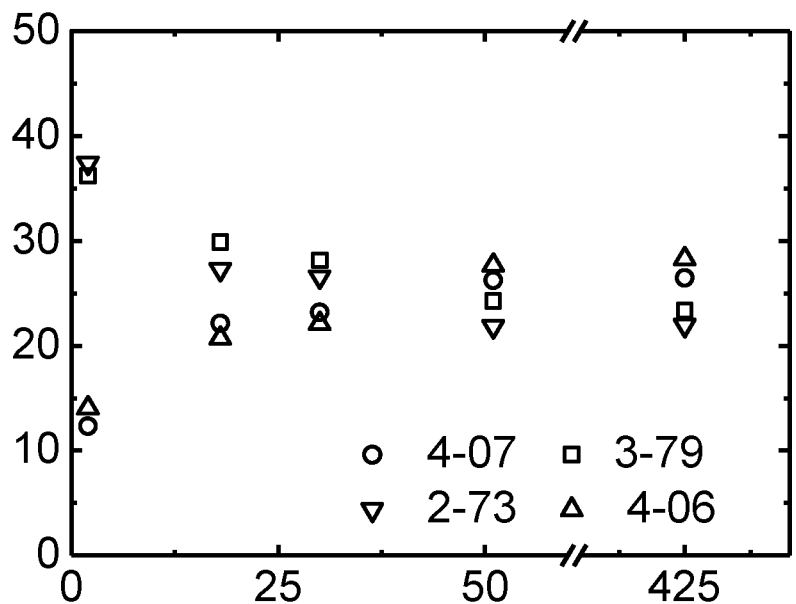

The evolution of the molar percentage (ordinate; without unit) of the different boronic esters in time (abscissa; minutes) during the metathesis between boronic esters containing respectively an aryldiol substituent and an alkyldiol substituent in anhydrous tetrahydrofuran at room temperature is displayed in FIG. 8.

2.6 Metathesis Between Boronic Esters Containing Respectively a 1,2-Alkydiol Substituent and a 1,3-Alkyldiol Substituent

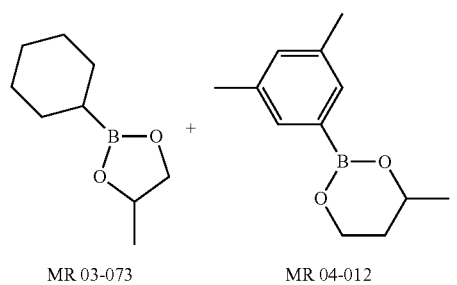

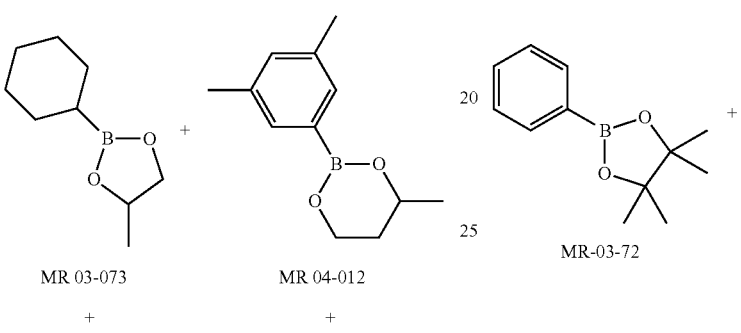

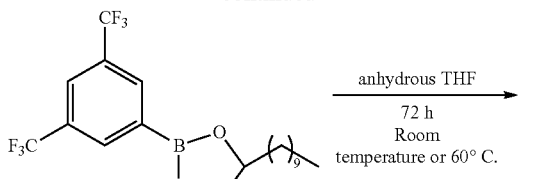

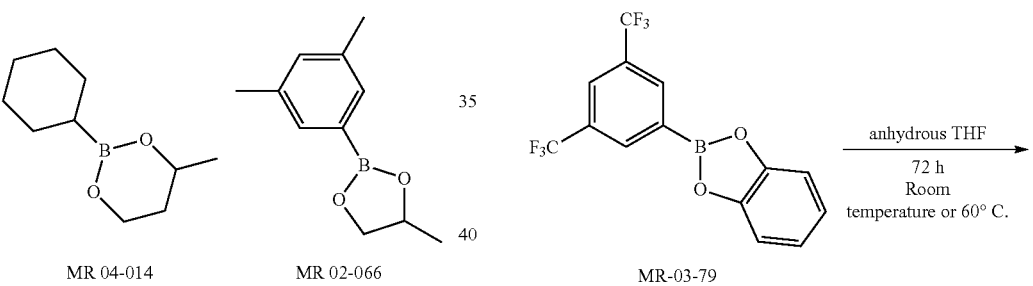

Figure 9:
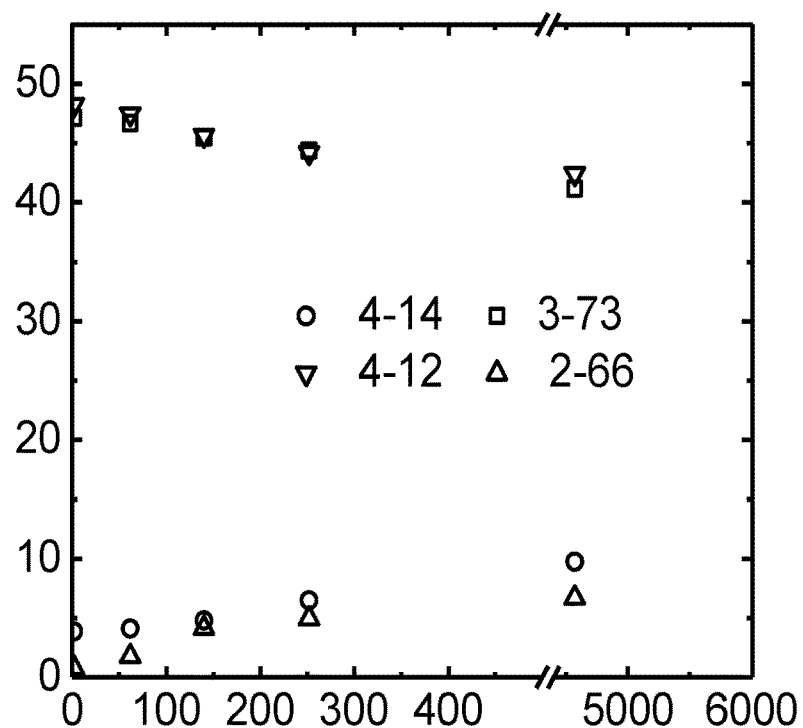

The evolution of the molar percentage (ordinate; without unit) of the different boronic esters in time (abscissa; minutes) during the metathesis between boronic esters containing respectively a 1,2-alkyldiol substituent and a 1,3-alkyldiol substituent in anhydrous tetrahydrofuran at room temperature is displayed in FIG. 9.

Comparative Example 1: Boronic Esters that do not Undergo Metathesis Reaction; Boronic Acids Pinacol Esters

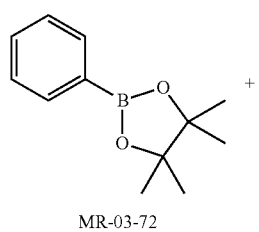

Example 3: Example of the Synthesis of a 9 Compound Library

Solutions of 3,5-dimethylphenylboronic acid 1,2-propanediol ester in anhydrous tetrahydrofuran (MR 02-066; 0.1 mmol per g of solvent), of 3,5-dichlorophenylboronic acid 1,2-hexanediol ester in anhydrous tetrahydrofuran (MR 02-073; 0.1 mmol per g of solvent), and of 3,5-bis(trifluoromethyl)phenylboronic acid 1,2-dodecanediol ester in anhydrous tetrahydrofuran (MR 02-071; 0.1 mmol per g of solvent) are simultaneously mixed together. The resulting solution is stirred at room temperature (RT) and the evolution of the concentration of the different components of the mixture is regularly monitored by gas chromatography.

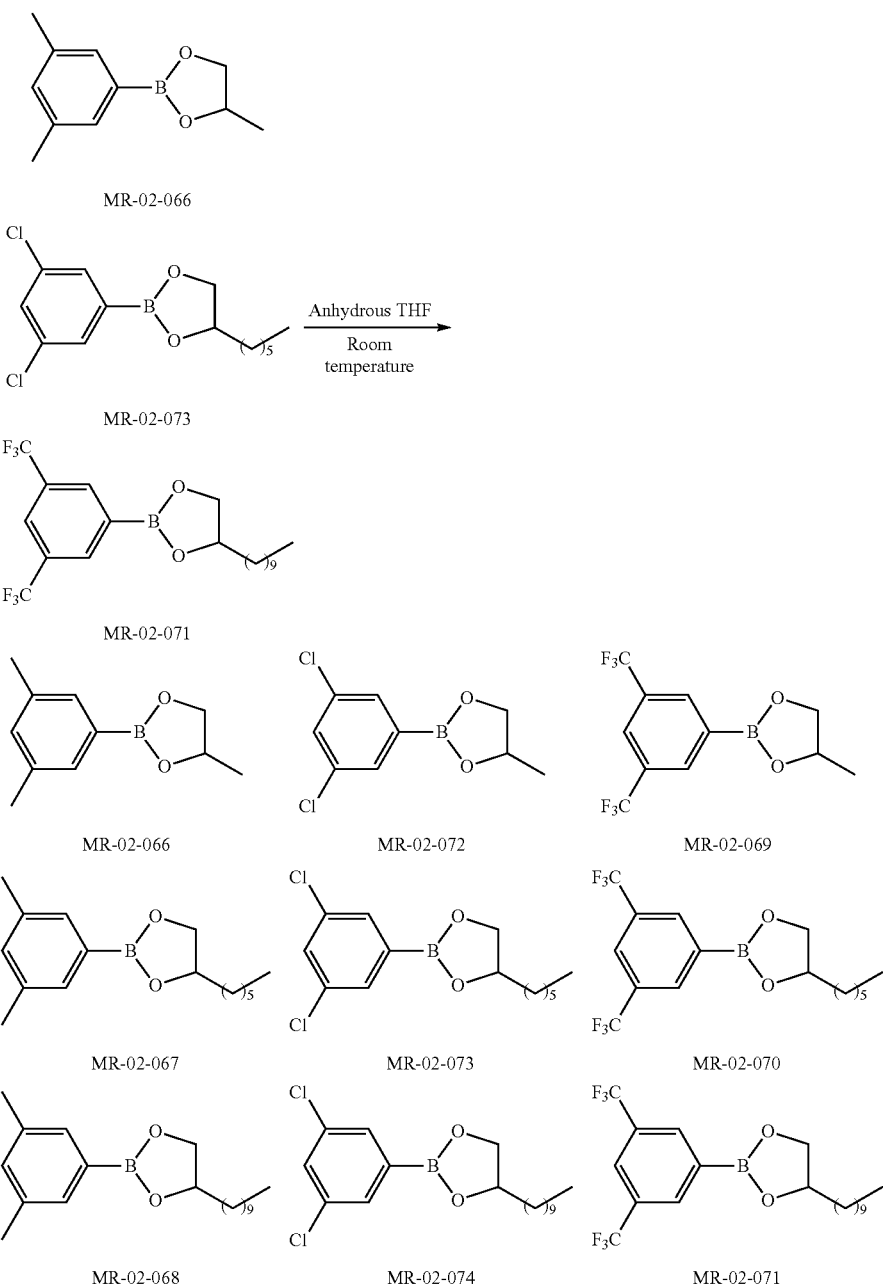

Figure 10:
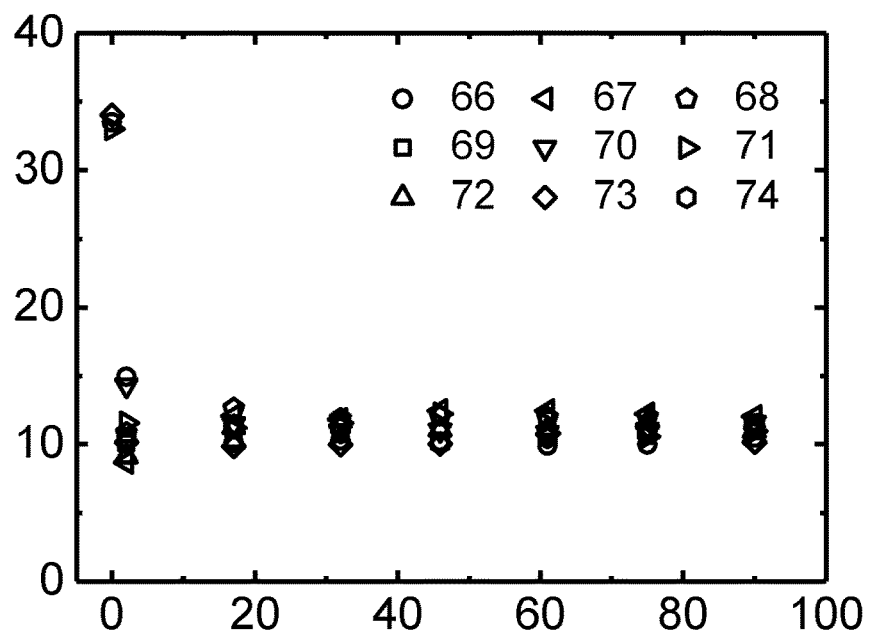

The evolution of the molar percentage (ordinate; without unit) of the different boronic esters as a function of time (abscissa; minutes) during the synthesis of a 9 compound library in anhydrous tetrahydrofuran at room temperature is displayed in FIG. 10.

Example 4: Example of the Synthesis of a 4 Compound Library and Evaluation of the Chemical Stability of the Components Towards Hydrolysis The following example illustrates the preparation of a 4 compound library by metathesis of boronic esters followed by the evaluation of the chemical stability of the compounds towards hydrolysis as a function of the substituents linked to the atoms of the dioxaborolane or dioxaborinane rings as well as the size of the boronic ester rings. In this way, with one single experiment and starting from 2 compounds only, it is possible to assess multiple parameters at once.

Solutions of phenylboronic acid 1,2-propanediol ester in anhydrous tetrahydrofuran (MR 05-026; 0.1 mmol per g of solvent) and of 3,5-dimethylphenylboronic acid 1,3-butanediol ester in anhydrous tetrahydrofuran (MR 04-012; 0.1 mmol per g of solvent), are mixed together. The resulting solution is stirred at room temperature (RT) and the evolution of the concentration of the different components of the mixture is regularly monitored by gas chromatography. After 48 hours of stirring at room temperature, a few equivalents of water as compared to boronic ester functions are added in successive steps to estimate the chemical stability of the different components of the library towards hydrolysis. The evolution of the concentration of the different components of the mixture is regularly monitored by gas chromatography.

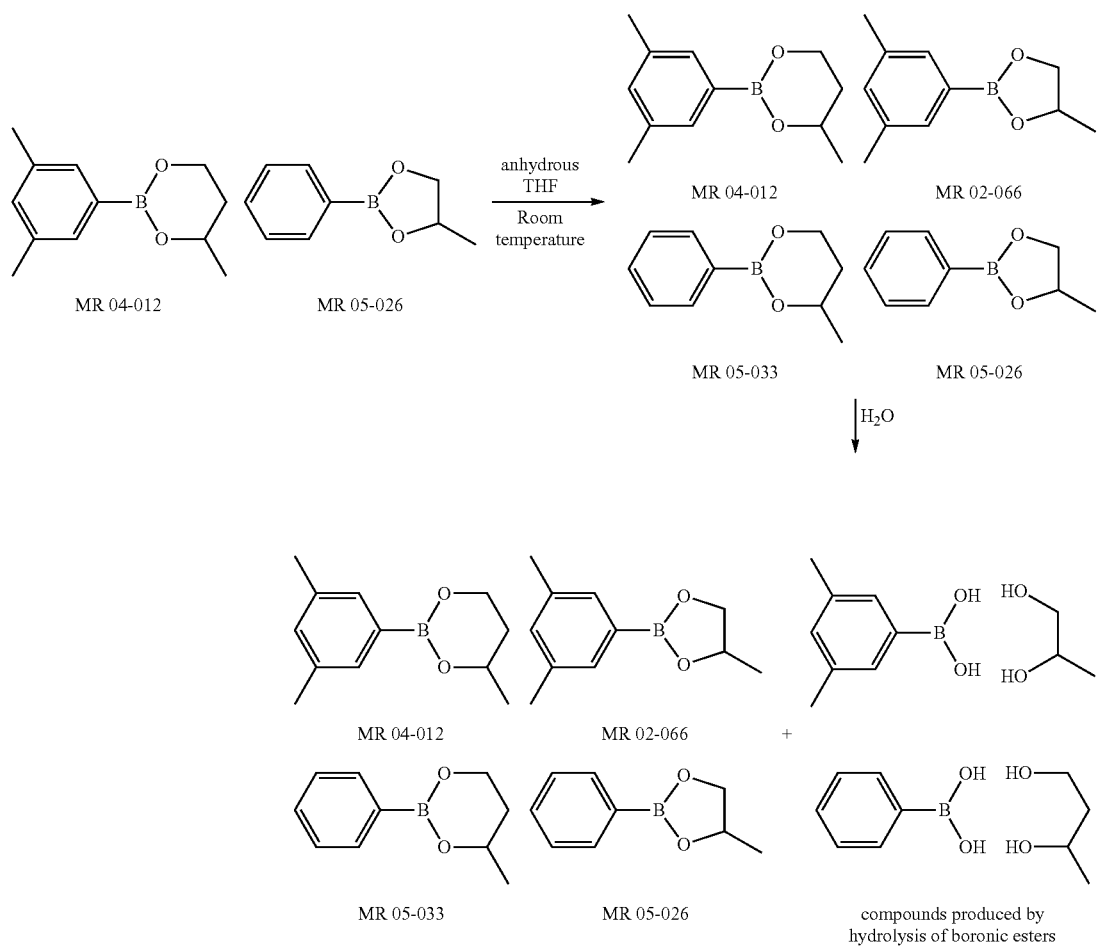

Table 1 recapitulates the molar equivalents of water successively added to the 4 compound library of boronic esters in order to estimate the chemical stability of the different components towards hydrolysis as a function of the substituents linked to the atoms of the dioxaborolane or dioxaborinane rings as well as the size of the boronic ester rings.

TABLE 1

| Step | Molar equivalents of water added per step in comparison to the initial number of boronic ester functions of all the components of the library [eq] | Molar equivalents of water added altogether in comparison to the initial number of boronic ester functions of all the components of the library [eq] | Concentration ($H_2O$) [mmol/mL] |
|---|---|---|---|
| a1 (t = 48 h + 48 min) | 0.25 | 0.25 | 0.044 |
| a2 (t = 48 h + 192 min) | 0.25 | 0.5 | 0.091 |
| b1 (t = 48 h + 348 min) | 0.5 | 1 | 0.185 |
| c1 (t = 48 h + 438 min) | 1 | 2 | 0.378 |
| c2 (t = 48 h + 1479 min) | 1 | 3 | 0.580 |
| d1 (t = 48 h + 1842 min) | 7 | 10 | 1.961 |

Table 2 shows the molar % of the 4 boronic ester compounds of the library before and after successive additions of water to the reaction mixture.

TABLE 2

| Step | MR 05-026 [%] | MR 05-033 [%] | MR 02-066 [%] | MR 04-012 [%] |
|---|---|---|---|---|
| t = 3 min; no water added | 52.7 | 0.16 | 0.54 | 46.6 |
| t = 23 h 55 min; no water added | 24.1 | 29.0 | 25.1 | 21.8 |
| t = 48 h 33 min; no water added | 23.7 | 29.4 | 23.7 | 23.2 |
| a1; t = 48 h + 48 min | 23.5 | 30.1 | 21.4 | 25.0 |
| a2; t = 48 h + 192 min | 22.8 | 30.4 | 21.1 | 25.8 |
| b1; t = 48 h + 348 min | 23.6 | 30.3 | 20.0 | 26.1 |
| c1; t = 48 h + 438 min | 23.5 | 31.0 | 19.0 | 26.5 |
| c2; t = 48 h + 1479 min | 23.6 | 30.3 | 18.4 | 27.7 |
| d1; t = 48 h + 1842 min | 24.6 | 30.4 | 17.5 | 27.5 |

This example illustrates the preparation of a 4 compound library by metathesis of boronic esters followed by the evaluation of the chemical stability of the compounds towards hydrolysis as a function of the substituents linked to the atoms of the dioxaborolane or dioxaborinane rings as well as the size of the boronic ester rings. This experiment illustrates the greater stability against hydrolysis of dioxaborinane rings as compared to dioxaborolane rings, as well as the influence of the radical linked the boron atom on the stability of boronic ester functions against hydrolysis. In this way, with one single experiment and starting from 2 compounds only, it is possible to assess multiple parameters that play a role on the stability and the chemical reactivity of a family of compounds.

Example 5: Metathesis Between Phenylboronic Esters in the Absence of Solvents and at Different Temperatures The following examples illustrate the fact that the metathesis of boronic esters can be conducted in bulk, i.e. in the absence of solvents, and in a large range of temperatures. The bulk metathesis of boronic esters was conducted at three different temperatures: 60° C., 85° C. and 150° C.

General procedure for the metathesis reaction of boronic esters in bulk and kinetic study by gas chromatography (GC):

Equimolar quantities of MR-2016a and MR-02-066 were mixed in an oven dried and argon-purged Schlenk flask and the reaction mixtures were kept under inert atmosphere and stirred at 60° C., respectively 85° C., respectively 150° C.

GC was conducted on a Shimadzu gas chromatograph GC-2014 equipped with a Zebron-5HT "inferno" column and helium as carrier gas. Injection was done manually by injecting 1 µL sample volumes using a 10 µL syringe from Hamilton (gastight 1701). Before running analysis the entire set-up was pre-heated to 350° C. and kept at constant carrier gas flow of 5 mL/min and split ratio of 2.0 for at least 30 minutes. Samples were analyzed with a flame ionization detector (FID). The following GC method was used for analysis of the exchange reactions: Tinjection/detector=350° C., Tcolumn=120° C., Tramp=30° C./min, carrier gas flow 5.0 mL/min and split ratio=2.0. Samples were taken with cleaned, dried and argon-purged needles and added to a small volume of dried DCM (dried, under argon) to dilute each sample mixture before injection.

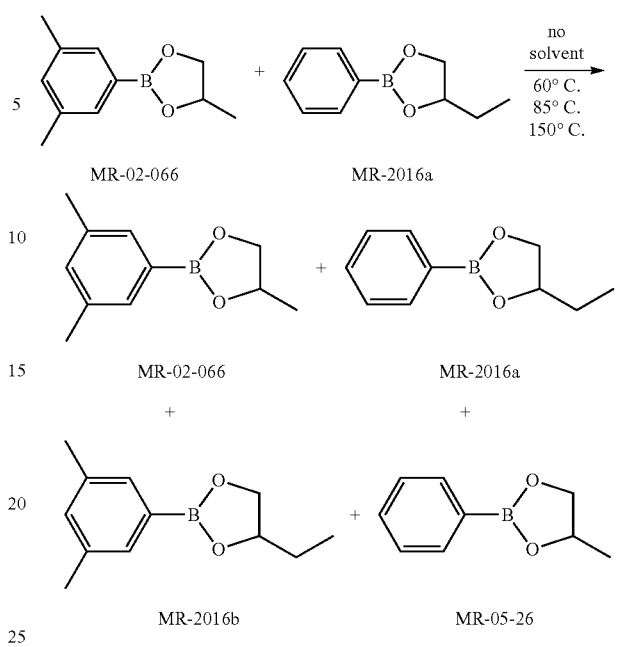

Figure 11:
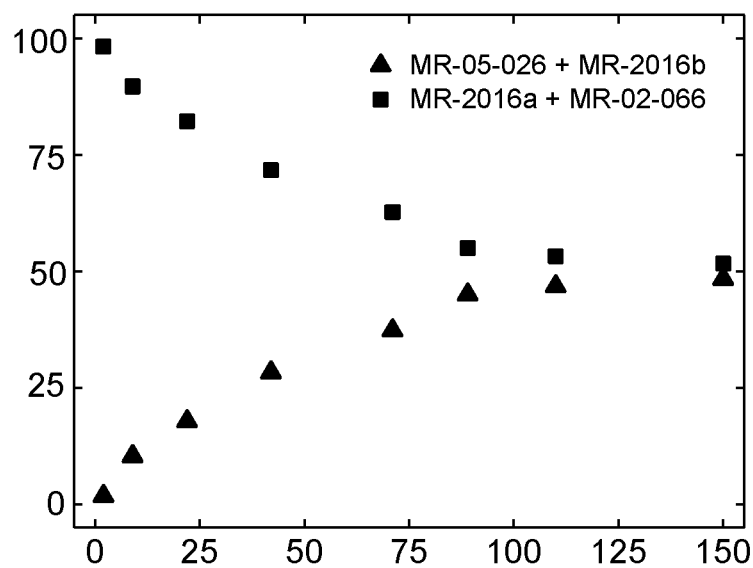
Figure 12:
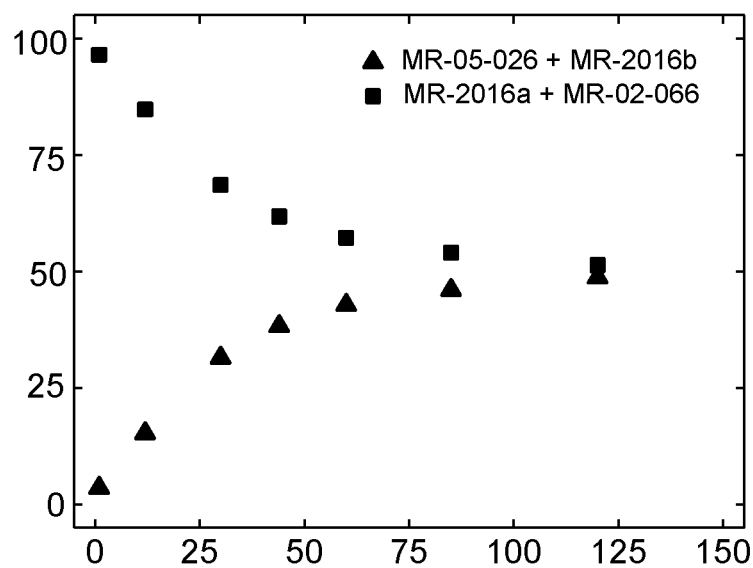
FIG. 12. Evolution of the molar percentage (ordinate; without unit) as a function of time (abscissa; minutes) of the two starting boronic esters and of the two boronic esters formed during the metathesis reaction of two phenylboronic esters in bulk at 85° C.
Figure 13:
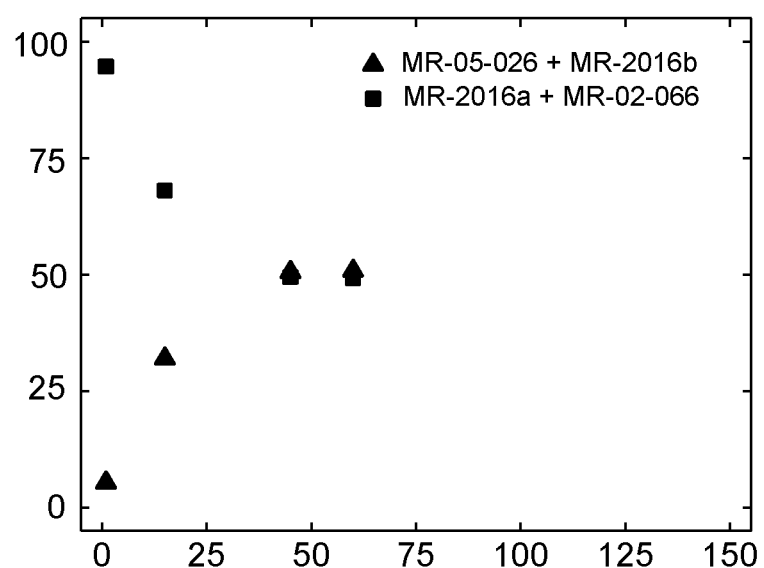
FIG. 13. Evolution of the molar percentage (ordinate; without unit) as a function of time (abscissa; minutes) of the two starting boronic esters and of the two boronic esters formed during the metathesis reaction of two phenylboronic esters in bulk at 150° C.

The evolution of the molar percentage (ordinate; without unit) of the two starting boronic esters and of the two boronic esters formed during the metathesis reaction of two phenylboronic esters in bulk:
- at 60° C. is plotted as a function of time (abscissa; minutes) in FIG. 11.
- at 85° C. is plotted as a function of time (abscissa; minutes) in FIG. 12.
- at 150° C. is plotted as a function of time (abscissa; minutes) in FIG. 13.

REFERENCES

1. Andreas HERMANN, Dynamic mixtures and combinatorial libraries: imines as probes for molecular evolution at the interface between chemistry and biology, Organic and Biomolecular Chemistry, 2009, 7, 3195-3204
2. Marco F. SCHIMIDT and Jörg RADEMANN, Dynamic template-assisted strategies in fragment-based drug discovery, Trends in Biotechnology, Vol. 27, No 9, 2009
3. Olof RAMSTROM and Jean-Marie LEHN, Drug discovery by dynamic combinatorial librairies, January 2002, Vol. 1
4. Hall, D. G., Boronic Acids—Preparation, Applications in Organic Synthesis and Medicine, WILEY-VCH: (2008). Editeur: Wiley VCH; Édition: 2nd Completely Revised Edition, 2 Volume Set (19 Oct. 2011). ISBN-10: 3527325980, ISBN-13: 978-3527325986

The invention claimed is:
1. A process for the preparation of a compound library, comprising the following steps:
   i) having available at least two different compounds each comprising at least a dioxaborolane or dioxaborinane ring, forming a boronic ester function, wherein in said compounds:
      the boron of the dioxaborolane or dioxaborinane ring is directly bonded to a carbon atom of a hydrocarbon radical;
      at least one carbon atom of the dioxaborolane or dioxaborinane ring is monosubstituted, the other carbon atoms of the dioxaborolane or dioxaborinane ring is non-substituted or monosubstituted;

in at least two compounds, the hydrocarbon radicals linked to the boron are different;

in at least two compounds, the substituents carried by at least one of the carbon atoms of the dioxaborolane or dioxaborinane rings are different and/or the size of the boronic ester ring is different; and ii) reacting the compounds of step (i) and forming, by a boronic ester metathesis reaction, the library comprising at least four different compounds, each having at least one substituents of a dioxaborolane or dioxaborinane ring different and/or a boronic ester ring of a different size compared to another compound, wherein step (ii) is carried out in an anhydrous solvent selected from the group consisting of alkanes, aromatic solvents, heterocycles, ethers, esters, ketones, amides, apolar aprotic solvents, halogenated solvents, heteroaromatic solvents, hydrocarbons, mineral oils, natural oils, synthetic oils, and a mixture of two or more of these solvents, and wherein step (ii) is carried out in the absence of detectable diol when analyzed by proton NMR, gas chromatography and infrared spectroscopy.

2. A process according to claim 1, wherein the library is prepared by a process comprising the following steps:

i) having available at least two compounds each comprising at least a dioxaborolane or dioxaborinane ring, of formula (Ia) and (Ib); and ii) reacting the compounds of step (i) and forming, by a boronic ester metathesis reaction, the library comprising at least four compounds of formula (Ia), (Ib), (Ic) and (Id)

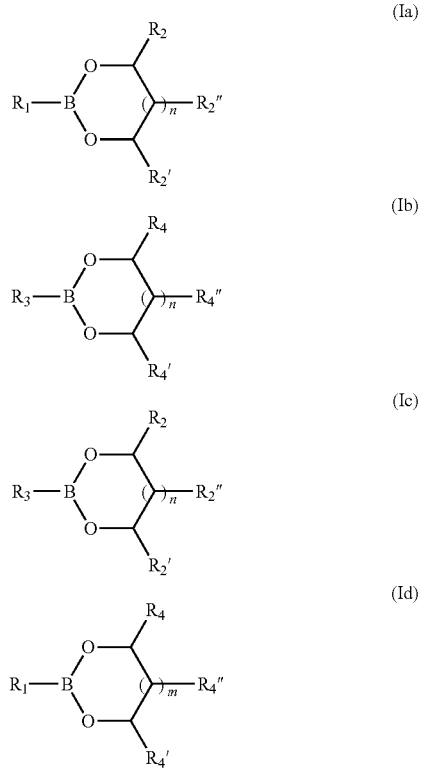

wherein:

n=0 or 1, m=0 or 1, $R_1$ and $R_3$ are different and each represents a hydrocarbon radical; the atom of $R_1$ and $R_3$ linked to the boron is a carbon atom, $R_2$, $R_2'$, and $R_2''$, identical or different, each represents a hydrogen atom, a hydrocarbon radical, or form together an aliphatic or aromatic ring, $R_4$, $R_4'$, and $R_4''$, identical or different, each represents a hydrogen atom, a hydrocarbon radical, or form together an aliphatic or aromatic ring, and If n=m then at least one of the substituents $R_4$, $R_4'$, and $R_4''$ is different from the substituents $R_2$, $R_2'$, and $R_2''$ and at least one carbon atom of the dioxaborolane or dioxaborinane ring of formula (Ia) and formula (Ib) is monosubstituted.

3. A process according to claim 1, wherein, in step (i), more than two compounds carrying at least one dioxaborolane or dioxaborinane ring are available.

4. A process according to claim 1, wherein, in step (i), at least one compound carrying several dioxaborolane or dioxaborinane rings is available.

5. A process according to claim 2, in which the reaction is carried out with more than two compounds (Ia) and (Ib) placed in the reaction mixture and different from one another: by their different $R_1$ groups or their different $R_3$ groups; and by their different $R_2$, $R_2'$, $R_2''$ groups or their different $R_4$, $R_4'$, $R_4''$ groups.

6. A process according to claim 1, wherein the reaction is carried out in an organic medium that is defavourable to the hydrolysis of the boronic esters of the dioxaborolane or dioxaborinane rings.

7. A process for the preparation of a compound library, comprising the following steps:

i) having available at least two different compounds each comprising at least a dioxaborolane or dioxaborinane ring, forming a boronic ester function, wherein in said compounds:

the boron of the dioxaborolane or dioxaborinane ring is directly bonded to a carbon atom of a hydrocarbon radical;

at least one carbon atom of the dioxaborolane or dioxaborinane ring is monosubstituted, the other carbon atoms of the dioxaborolane or dioxaborinane ring is non-substituted or monosubstituted;

in at least two compounds, the hydrocarbon radicals linked to the boron are different;

in at least two compounds, the substituents carried by at least one of the carbon atoms of the dioxaborolane or dioxaborinane rings are different and/or the size of the boronic ester ring is different; and ii) reacting the compounds of step (i) and forming, by a boronic ester metathesis reaction, the library comprising at least four different compounds, each having at least one substituents of a dioxaborolane or dioxaborinane ring different and/or a boronic ester ring of a different size compared to another compound, wherein step (ii) is carried out in the absence of solvents.

8. A process according to claim 1, wherein step (ii) is carried out in the absence of catalyst.

9. A process according to claim 1, wherein step (ii) is carried out at a temperature of between 0° C. and 60° C.

10. A process according to claim 1, wherein at least one of the compounds of step (i) comprises a centre of asymmetry.

11. A process according to claim 1, wherein the compounds of step (i) are peptides comprising at least one dioxaborolane or dioxaborinane group.

12. A process according to claim 1, wherein the dioxaborolane groups of step (i) are prepared from 1,2-diols and the dioxaborinane groups of step (i) are prepared from 1,3-diols.

13. A process according to claim 2, wherein $R_1$, $R_2$, $R_2'$, $R_2''$, $R_3$, $R_4$, $R_4'$ and $R_4''$ are independently chosen from among alkyl, alkenyl, alkynyl, halogenoalkyl, cycloalkyl, polycycloalkyl, cycloheteroalkyl, polycycloheteroalkyl, aryl, cycloheteroaryl, polyaryl, polycycloheteroaryl, aralkyl or alkyl-aryl radicals; each of these radicals may be substituted with one or more radicals chosen from among halogens, —OH, —NH$_2$, —NHRz, —NRzR'z, —C(O)—H, —C(O)—Rz, —C(O)—OH, —C(O)—O-Rz, —O—C(O)—Rz, —O—C(O)—O-Rz, —O—C(O)—N(H)—Rz, —N(H)—C(O)—O-Rz, —O-Rz, —SH, —S-Rz, —S—S-Rz, —CO—NH$_2$, —C(O)—N(H)—Rz, —C(O)—NRzR'z, —N(H)—C(O)—Rz, —N(Rz)-C(O)—Rz', —CN, —NCO, —NCS, boronic esters, alkyls, alkenyls, alkynyls, halogenoalkyls, cycloalkyls, polycycloalkyls, cycloheteroalkyls, polycycloheteroalkyls, aryls, cycloheteroaryls, polyaryls, polycycloheteroaryles, aralkyls, alkyl-aryls, and heteroaralkyls, with Rz and R'z, identical or different, representing a hydrocarbon radical.

14. A process according to claim 2, wherein $R_2$, $R_2'$, $R_2''$, $R_4$, $R_4'$ and $R_4''$ are chosen from among H or an alkyl, alkenyl, alkynyl or halogenoalkyl radical.

15. A process according to claim 1, wherein following the preparation of a compound library, an evaluation step of the activity of the compounds in the library is carried out.

16. A process according to claim 7, wherein the library is prepared by a process comprising the following steps:
(i) having available at least two compounds each comprising at least a dioxaborolane or dioxaborinane ring, of formula (Ia) and (Ib);
(ii) reacting the compounds of step (i) and forming, by a boronic ester metathesis reaction, the library comprising at least four compounds of formula (Ia), (Ib), (Ic) and (Id)

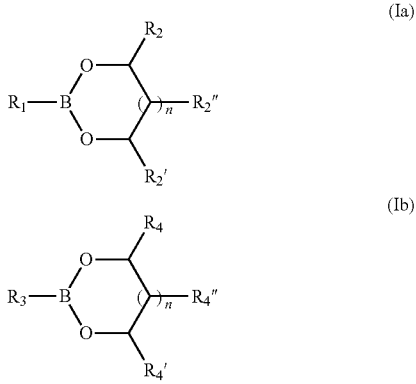

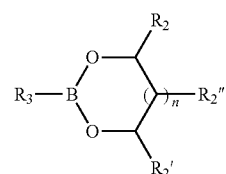

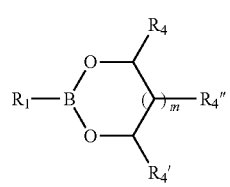

wherein
n=0 or 1,
m=0 or 1,
$R_1$ and $R_3$ are different and each represents a hydrocarbon radical; the atom of $R_1$ and $R_3$ linked to the boron is a carbon atom,
$R_2$, $R_2'$, and $R_2''$, identical or different, each represents a hydrogen atom, a hydrocarbon radical, or form together an aliphatic or aromatic ring,
$R_4$, $R_4'$, and $R_4''$, identical or different, each represents a hydrogen atom, a hydrocarbon radical, or form together an aliphatic or aromatic ring, and
If n=m then at least one of the substituents $R_4$, $R_4'$, and $R_4''$ is different from the substituents $R_2$, $R_2'$, and $R_2''$
and at least one carbon atom of the dioxaborolane or dioxaborinane ring of formula (Ia) and formula (Ib) is monosubstituted.

17. A process according to claim 16, wherein $R_1$, $R_2$, $R_2'$, $R_2''$, $R_3$, $R_4$, $R_4'$ and $R_4''$ are independently chosen from among alkyl, alkenyl, alkynyl, halogenoalkyl, cycloalkyl, polycycloalkyl, cycloheteroalkyl, polycycloheteroalkyl, aryl, cycloheteroaryl, polyaryl, polycycloheteroaryl, aralkyl or alkyl-aryl radicals; each of these radicals may be substituted with one or more radicals chosen from among halogens, —OH, —NH$_2$, —NHRz, —NRzR'z, —C(O)—H, —C(O)—Rz, —C(O)—OH, —C(O)—O-Rz, —O—C(O)—Rz, —O—C(O)—O-Rz, —O—C(O)—N(H)—Rz, —N(H)—C(O)—O-Rz, —O-Rz, —SH, —S-Rz, —S—S-Rz, —CO—NH$_2$, —C(O)—N(H)—Rz, —C(O)—NRzR'z, —N(H)—C(O)—Rz, —N(Rz)-C(O)—Rz', —CN, —NCO, —NCS, boronic esters, alkyls, alkenyls, alkynyls, halogenoalkyl s, cycloalkyl s, polycycloalkyls, cycloheteroalkyls, polycycloheteroalkyls, aryls, cycloheteroaryls, polyaryls, polycycloheteroaryles, aralkyls, alkyl-aryls, and heteroaralkyls, with Rz and R'z, identical or different, representing a hydrocarbon radical.

18. A process according to claim 16, wherein $R_2$, $R_2'$, $R_2''$, $R_4$, $R_4'$ and $R_4''$ are chosen from among H or an alkyl, alkenyl, alkynyl or halogenoalkyl radical.

* * * * *